US009156806B2

(12) United States Patent
Shaikh et al.

(10) Patent No.: US 9,156,806 B2
(45) Date of Patent: *Oct. 13, 2015

(54) PROCESS FOR PURIFYING CRUDE FURAN 2,5-DICARBOXYLIC ACID USING HYDROGENATION

(71) Applicant: Eastman Chemical Company, Kingsport, TN (US)

(72) Inventors: Ashfaq Schahanawaz Shaikh, Kingsport, TN (US); Kenny Randolph Parker, Afton, TN (US); Mesfin Ejerssa Janka, Kingsport, TN (US); Lee Reynolds Partin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/259,754

(22) Filed: Apr. 23, 2014

(65) Prior Publication Data

US 2014/0235880 A1     Aug. 21, 2014

Related U.S. Application Data

(63) Continuation of application No. 13/758,070, filed on Feb. 4, 2013, now Pat. No. 8,748,479.

(60) Provisional application No. 61/663,237, filed on Jun. 22, 2012.

(51) Int. Cl.
*A61K 31/341* (2006.01)
*C07D 307/34* (2006.01)
*C07D 307/68* (2006.01)

(52) U.S. Cl.
CPC .................................. *C07D 307/68* (2013.01)

(58) Field of Classification Search
CPC ............................ A61K 31/341; C07D 307/34
USPC ........................................... 549/485; 514/448
See application file for complete search history.

(56) References Cited

U.S. PATENT DOCUMENTS

| | | | |
|---|---|---|---|
| 2,797,197 A | 6/1957 | Thompson et al. | |
| 3,203,963 A | 8/1965 | Hales et al. | |
| 3,326,944 A | 6/1967 | Lew | |
| 4,977,283 A | 12/1990 | Leupold et al. | |
| 6,737,481 B1 | 5/2004 | Kurian et al. | |
| 7,052,764 B2 | 5/2006 | Chang et al. | |
| 7,385,081 B1 | 6/2008 | Gong | |
| 7,411,078 B2 | 8/2008 | Miura et al. | |
| 7,572,925 B2 | 8/2009 | Dumesic et al. | |
| 7,700,788 B2 | 4/2010 | Lilga et al. | |
| 8,183,020 B2 | 5/2012 | Hanke | |
| 8,193,381 B2 | 6/2012 | Lilga et al. | |
| 8,193,382 B2 | 6/2012 | Lilga et al. | |
| 8,748,479 B2 * | 6/2014 | Shaikh et al. ................. 514/448 |
| 2003/0055271 A1 | 3/2003 | Grushin et al. | |
| 2006/0205977 A1 | 9/2006 | Sumner, Jr. et al. | |
| 2007/0232815 A1 | 10/2007 | Miura et al. | |
| 2009/0124829 A1 | 5/2009 | Gong | |
| 2009/0131690 A1 | 5/2009 | Gruter et al. | |
| 2009/0156841 A1 | 6/2009 | Sanborn et al. | |
| 2009/0326262 A1 | 12/2009 | Wan | |
| 2010/0210867 A1 | 8/2010 | Bustamante et al. | |
| 2011/0092720 A1 | 4/2011 | Yutaka et al. | |

FOREIGN PATENT DOCUMENTS

| | | |
|---|---|---|
| CS | 87340 | 7/1959 |
| EP | 1 834 951 A1 | 9/2007 |
| EP | 2 197 868 B1 | 4/2011 |
| EP | 2 197 865 B1 | 8/2012 |
| JP | 2007-261986 A | 10/2007 |
| JP | 2007-261990 A | 10/2007 |
| JP | 2009-001519 A | 1/2009 |
| JP | 2009-013079 A | 1/2009 |
| JP | 2009-242312 A | 10/2009 |
| SU | 162962 A | 9/1962 |
| WO | WO 02/098836 A1 | 12/2002 |
| WO | WO 2007/092183 A2 | 8/2007 |
| WO | WO 2008/054804 A2 | 5/2008 |
| WO | WO 2009/023174 A2 | 2/2009 |
| WO | WO 2009/030506 A4 | 3/2009 |
| WO | WO 2009/030507 A4 | 3/2009 |
| WO | WO 2010/077133 A1 | 7/2010 |
| WO | WO 2010/132740 A2 | 11/2010 |
| WO | WO 2011/043660 A2 | 4/2011 |
| WO | WO 2012/161968 A1 | 11/2012 |

OTHER PUBLICATIONS

Copending U.S. Appl. No. 14/259,754, filed Apr. 23, 2014, Ashfaq Shaikh et al.

Notice of Allowance dated May 13, 2014 received in co-pending U.S. Appl. No. 13/758,088.

(Continued)

*Primary Examiner* — Golam M M Schameem

(74) *Attorney, Agent, or Firm* — Phan Law Group PLLC

(57) ABSTRACT

A process to produce a dry purified furan-2,5-dicarboxylic acid (FDCA) is described. After oxidation of 5-(hydroxymethyl)furfural (5-HMF), a crude FDCA stream is produced that is fed to a crystallization zone followed by a solid-liquid displacement zone to form a low impurity slurry stream. The solids in the low impurity slurry stream are dissolved in a dissolution zone to produce a hydrogenation feed that is hydrogenated in a hydrogenation reactor to generate a hydrogenated FDCA composition. The hydrogenated FDCA composition is routed to a crystallization zone to form a crystallized produce stream that is separated from liquid in a solid-liquid separation zone to generate a purified wet cake stream containing FDCA that can be dried in a drying zone to generate a dry purified FDCA product stream.

10 Claims, 2 Drawing Sheets

(56) References Cited

OTHER PUBLICATIONS

Copending U.S. Appl. No. 14/282,360, filed May 20, 2014, Janka et al.
Office Action dated Apr. 25, 2014 received in co-pending U.S. Appl. No. 13/228,797.
Office Action dated Apr. 25, 2014 received in co-pending U.S. Appl. No. 13/228,809.
Notice of Allowance dated Apr. 28, 2014 received in co-pending U.S. Appl. No. 13/228,803.
Notice of Allowance dated Apr. 28, 2014 received in co-pending U.S. Appl. No. 13/228,813.
Office Action dated Apr. 30, 2014 received in co-pending U.S. Appl. No. 13/798,235.
Notice of Allowance dated May 1, 2014 received in co-pending U.S. Appl. No. 13/228,799.
Office Action dated May 29, 2014 received in co-pending U.S. Appl. No. 13/228,816.
Notice of Allowance dated Jun. 11, 2014 received in co-pending U.S. Appl. No. 13/553,976.
Copending U.S. Appl. No. 14/309,010, filed Jun. 19, 2014, Janka et al.
Copending U.S. Appl. No. 14/317,588, filed Jun. 27, 2014, Parker et al.
Copending U.S. Appl. No. 14/317,692, filed Jun. 27, 2014, Janka et al.
Copending U.S. Appl. No. 14/317,782, filed Jun. 27, 2014, Parker et al.
Copending U.S. Appl. No. 14/317,875, filed Jun. 27, 2014, Janka et al.
Slavinskaya, V. A., et al., "Liquid-Phase Catalytic Oxidation of 5-Methylfurfural," React. Kinet. Catal. Lett., 1979, vol. 11, No. 3, pp. 215-220.
Gandini, A., et al., "Rapid Communication: The Furan Counterpart of Poly(ethylene terephthalate): An Alternative Material Based on Renewable Resources," Journal of Polymer Science: Part A: Polymer Chemistry, 2009, vol. 47, pp. 295-298, Wiley Periodicals, Inc.
Partenheimer, W. et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts," Adv. Synth. Catal., 2001, vol. 343, No. 1, pp. 102-111.
Lewkowski, J.; "Synthesis, Chemistry and Applications of 5-Hydroxymethylfurfural and its Derivatives," ARKIVOC, 2001, pp. 17-54.
Zakharov, I. V., "Mechanism of Initiation and Inhibition by Mn(II) in Hydrocarbon Oxidation in the Presence a Cobalt-Manganese Bromide Catalyst," Kinetics and Catalysis, 1998, vol. 39, No. 4, pp. 485-492.
Jiao, X. J. et al., "Kinetics of Manganese(III) Acetate in Acetic Acid: Generation of Mn(III) with Co(III), Ce(IV), and Dibromide Radicals; Reactions of Mn(III) with Mn(II), Co(II), Hydrogen Bromide, and Alkali Bromides," Inorg. Chem., 2000, vol. 39, pp. 1549-1554, American Chemical Society.
Copending U.S. Appl. No. 13/228,816, filed Sep. 9, 2011, Mesfin Ejerssa Janka, et al.
Copending U.S. Appl. No. 13/228,799, filed Sep. 9, 2011, Mesfin Ejerssa Janka, et al.
Copending U.S. Appl. No. 13/228,809, filed Sep. 9, 2011, Mesfin Ejerssa Janka, et al.
Copending U.S. Appl. No. 13/228,803, filed Sep. 9, 2011, Mesfin Ejerssa Janka, et al.
Copending U.S. Appl. No. 13/228,797, filed Sep. 9, 2011, Mesfin Ejerssa Janka, et al.
Copending U.S. Appl. No. 13/228,813, filed Sep. 9, 2011, Ashfaq Shaikh, et al.
PCT International Search Report and Written Opinion dated Jul. 27, 2012 for International Application No. PCT/US2012/037223.
PCT International Search Report and Written Opinion dated Aug. 7, 2012 for International Application No. PCT/US2012/037218.
PCT International Search Report and Written Opinion dated Jul. 27, 2012 for International Application No. PCT/US2012/037204.
PCT International Search Report and Written Opinion dated Jul. 27, 2012 for International Application No. PCT/US2012/037206.
PCT International Search Report and Written Opinion dated Aug. 3, 2012 for International Application No. PCT/US2012/037210.
Copending U.S. Appl. No. 13/553,976, filed Jul. 20, 2012, Mesfin Ejerssa Janka, et al.
PCT International Search Report and Written Opinion dated Aug. 23, 2012 for International Application No. PCT/US2012/037228.
Chheda et al., "Production of 5-hydromethylfurfural and furfural by dehydration of biomass-derived mono- and poly-saccharides." Green Chemistry, vol. 9, pp. 342-350 (2007).
Werpy et al., "Top Value Added Chemicals from Biomass" DOE (Pacific NW National Laboratory) (Aug. 2004).
Verevkin et al., "Biomass-Derived Platform Chemicals: Thermodynamic Studies on the Conversion of 5-Hydroxymethylfurfural into Bulk Intermediates" Ind. Eng. Chem. Res., vol. 48, pp. 10087-10093 (2009).
Manasek, Z., "Modification of a Fiber-Forming Polyester Based on 2,5-Furandicarboxylic Acid", Mar. 20, 1963, pp. 35-38, UDC 677. 465.
Rodivilova et al., "Synthesis and Investigation of Polyarylates Based on 2,5-Furandicarboxylic Acid and Diphenylolpropane", Khimiya I Khimicheskaya Tekhnologiya, No. 7, 1968, pp. 818-821.
Copending U.S. Appl. No. 13/758,070, filed Feb. 4, 2013, Kenny Randolph Parker, et al.
Copending U.S. Appl. No. 13/758,080, filed Feb. 4, 2013, Mesfin Ejerssa Janka, et al.
Office Action dated Apr. 18, 2013 received in co-pending U.S. Appl. No. 13/228,797.
Office Action dated Apr. 18, 2013 received in co-pending U.S. Appl. No. 13/228,813.
Office Action dated Apr. 29, 2013 received in co-pending U.S. Appl. No. 13/228,799.
Office Action dated May 31, 2013 received in co-pending U.S. Appl. No. 13/228,803.
Office Action dated Jun. 6, 2013 received in co-pending U.S. Appl. No. 13/228,809.
Office Action dated Jun. 6, 2013 received in co-pending U.S. Appl. No. 13/228,816.
PCT International Search Report and Written Opinion dated Jul. 29, 2013 for International Application No. PCT/US2013/044935.
PCT International Search Report and Written Opinion dated Aug. 9, 2013 for International Application No. PCT/US2013/044932.
Office Action dated Sep. 30, 2013 received in co-pending U.S. Appl. No. 13/758,070.
Office Action dated Sep. 30, 2013 received in co-pending U.S. Appl. No. 13/758,080.
Moldenhauer, et al., "Beitrage zur Furanchemie I", Justus Liebigs Annalen Der Chemie, vol. 580, 1953, pp. 169-190.
Office Action dated Oct. 25, 2013 received in co-pending U.S. Appl. No. 13/228,813.
PCT International Search Report and Written Opinion dated Oct. 31, 2013 for International Application No. PCT/US2013/050799.
Office Action dated Nov. 5, 2013 received in co-pending U.S. Appl. No. 13/228,797.
Office Action dated Nov. 8, 2013 received in co-pending U.S. Appl. No. 13/228,803.
Office Action dated Nov. 8, 2013 received in co-pending U.S. Appl. No. 13/758,070.
Office Action dated Nov. 12, 2013 received in co-pending U.S. Appl. No. 13/228,799.
Office Action dated Nov. 14, 2013 received in co-pending U.S. Appl. No. 13/228,809.
Office Action dated Nov. 18, 2013 received in co-pending U.S. Appl. No. 13/758,088.
Copending U.S. Appl. No. 14/084,165, filed Nov. 19, 2013, Ashfaq Shaikh et al.
PCT International Search Report and Written Opinion dated Nov. 28, 2013 for International Application No. PCT/US2013/050794.
Office Action dated Dec. 13, 2013 received in co-pending U.S. Appl. No. 13/228,816.

(56) References Cited

OTHER PUBLICATIONS

Office Action dated Dec. 16, 2013 received in co-pending U.S. Appl. No. 13/553,976.
Notice of Allowance dated Apr. 1, 2014 received in co-pending U.S. Appl. No. 13/758,080.
Notice of Allowance dated Apr. 1, 2014 received in co-pending U.S. Appl. No. 13/758,070.
Office Action dated Apr. 17, 2014 received in co-pending U.S. Appl. No. 13/758,072.

* cited by examiner

PROCESS FOR PURIFYING CRUDE FURAN 2,5-DICARBOXYLIC ACID USING HYDROGENATION

CROSS-REFERENCE TO RELATED APPLICATIONS

This application is a continuation of U.S. patent application Ser. No. 13/758,070, filed 4 Feb. 2014, which in turn claims the benefit of U.S. Provisional Patent Application Ser. No. 61/663,237, filed 22 Jun. 2012. The entire disclosures of these documents are herein incorporated by reference.

FIELD OF THE INVENTION

This invention relates generally to the production of purified furan 2,5-dicarboxylic acids. In particular, the invention relates to a process for the purification of crude furan 2,5-dicarboxylic acid utilizing solid liquid separation, mild hydrogenation, and isolation techniques.

BACKGROUND OF THE INVENTION

Aromatic dicarboxylic acids such as terephthalic acid and isophthalic acid are used to produce a variety of polyester products, important examples of which are poly (ethylene terephthalate) and its copolymers. These aromatic dicarboxylic acids are synthesized by the catalyzed autoxidation of the corresponding dialkyl aromatic compounds which are obtained from fossil fuels (US 2006/0205977 A1). There is a growing interest in the use of renewable resources as feed stocks for the chemical industries mainly due to the progressive reduction of fossil reserves and their related environmental impacts.

Furan 2,5-dicarboxylic acid ("FDCA") is a versatile intermediate considered as a promising closest biobased alternative to terephthalic acid and isophthalic acid. It is synthesized by the catalytic oxidation of 5-(hydroxymethyl)furfural (5-HMF) as shown in equation 1 below; or by the catalytic oxidation of 5-HMF esters (5-R(CO)OCH$_2$-furfural where R=alkyl, cycloalkyl and aryl) as shown in equation 2 below; or by the catalytic oxidation of 5-HMF ethers (5-R'OCH$_2$-furfural, where R'=alkyl, cycloalkyl and aryl) as shown in equation 3 below; or by the catalytic oxidation of 5-alkyl furfurals (5-R"-furfural, where R"=alkyl, cycloalkyl and aryl) as shown in equation 4 below; in each case using a Co/Mn/Br catalyst system. Mixed feedstocks of 5-HMF and 5-HMF esters, mixed feedstocks of 5-HMF and 5-HMF ethers, and mixed feedstocks of 5-HMF and 5-alkyl furfurals can also be used.

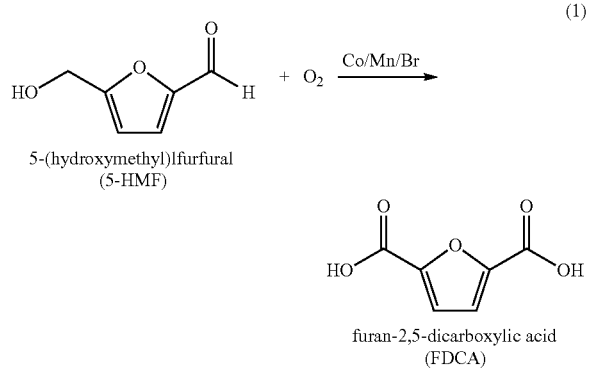

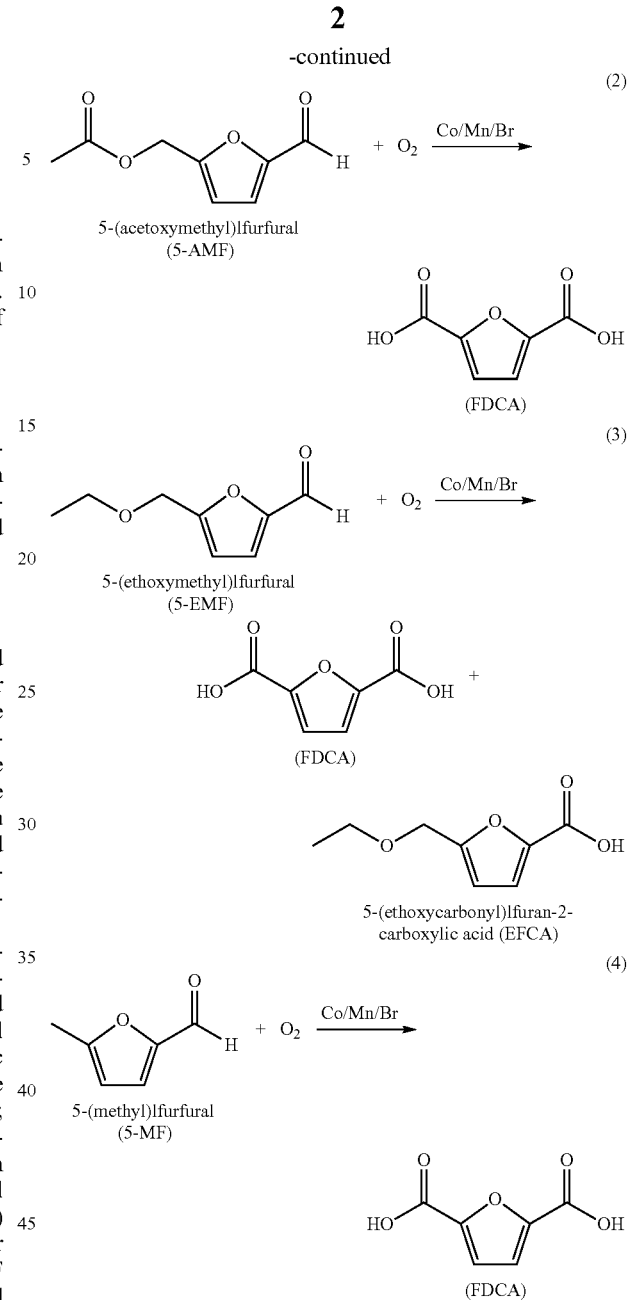

We have found that the above reactions work well. However a number of impurities are produced, particularly mono-carboxylic acid species such as 5-formyl furan-2-carboxyic acid (FFCA). These mono-carboxylic acids are not desirable since they terminate the chain growth of a polymer resulting in lower polymer viscosity. If colored bodies are present in the crude FDCA or remaining in the purified FDCA, these colored bodies carry through to compounds or polymers using the FDCA as a reactive monomer to thereby color the compound or polymer. Therefore, it is necessary to purify the crude FDCA to remove the color bodies while minimizing the presence of FFCA in the purified FDCA.

FDCA has been prepared by oxidation of 5-(hydroxymethyl) furfural (5-HMF) under air using homogenous catalysts (US2003/0055271 A1 and Partenheimer, W.; Grushin, V. V. *Adv. Synth. Catal.* 2001, 343, 102-111.) but only a maximum of 44.8% yield using Co/Mn/Br catalysts system and a maximum of 60.9% yield was reported using Co/Mn/Br/Zr catalysts combination. Heterogeneous catalysis oxidation of 5-HMF using $ZrO_2$ mixed with platinum (II) acetylacetonate in water has been reported in U.S. Pat. No. 7,700,788 B2, but due to very low solubility of FDCA in water, this process needs to be conducted under very dilute conditions to avoid precipitation of FDCA on the catalysts surface which makes the process not economical. Another heterogeneous catalysis oxidation of 5-HMF is reported in U.S. Pat. No. 4,977,283 using molecular $O_2$ and a Pt/C catalyst. High FDCA yield was achieved but at the extra expense of feeding purified $O_2$ and continually adjusting pH via sodium hydroxide addition. The reaction product was the disodium salt of FDCA leading to a wasteful salt by-product in the conversion to FDCA.

There remains a need to produce a FDCA at high yields and isolate purified FDCA product that has low color.

SUMMARY OF THE INVENTION

In this invention we disclose a process to make purified FDCA (pFDCA) by catalytic hydrogenation of a solvated FDCA composition under mild conditions.

In particular there is now provided a process for purifying a crude furan 2,5-dicarboxylic acid composition (cFDCA) comprising:
a) providing a cFDCA composition comprising furan 2,5-dicarboxylic acid (FDCA) solids, 5-formyl furan-2-carboxylic acid (FFCA), and a liquid oxidation solvent composition;
b) separating at least a portion of the oxidation solvent from the FDCA solids in the cFDCA composition in to generate a concentrated cFDCA composition comprising FDCA solids and enriched in the concentration of solids relative to the concentration of solids in the cFDCA composition fed to the solid-liquid separation zone;
c) feeding the concentrated cFDCA composition to a dissolution zone in which a hydrogenation solvent composition is combined with the FDCA solids in the concentrated cFDCA composition and dissolving at least a portion of said FDCA solids to thereby produce a solvated FDCA composition (sFDCA) comprising dissolved furan 2,5-dicarboxylic acid (FDCA), a hydrogenation solvent, and 5-formyl furan-2-carboxyic acid (FFCA);
c) subjecting the sFDCA composition to a hydrogenation reaction in a hydrogenation reaction zone under conditions sufficient to cause hydrogenation of at least a portion of FFCA in the sFDCA composition to generate a hydrogenated FDCA composition (hFDCA) comprising dissolved FDCA and the hydrogenation solvent; and
e) crystallizing the hFDCA composition to generate a crystallized hFDCA composition comprising liquid and FDCA solids; and
f) separating at least a portion of the liquid from the FDCA solids in the crystallized hFDCA composition to thereby generate a concentrated hFDCA composition enriched in the concentration of FDCA solids relative to the concentration of FDCA solids in the crystallized hFDCA composition.

DETAILED DESCRIPTION OF THE INVENTION

Figure 1:
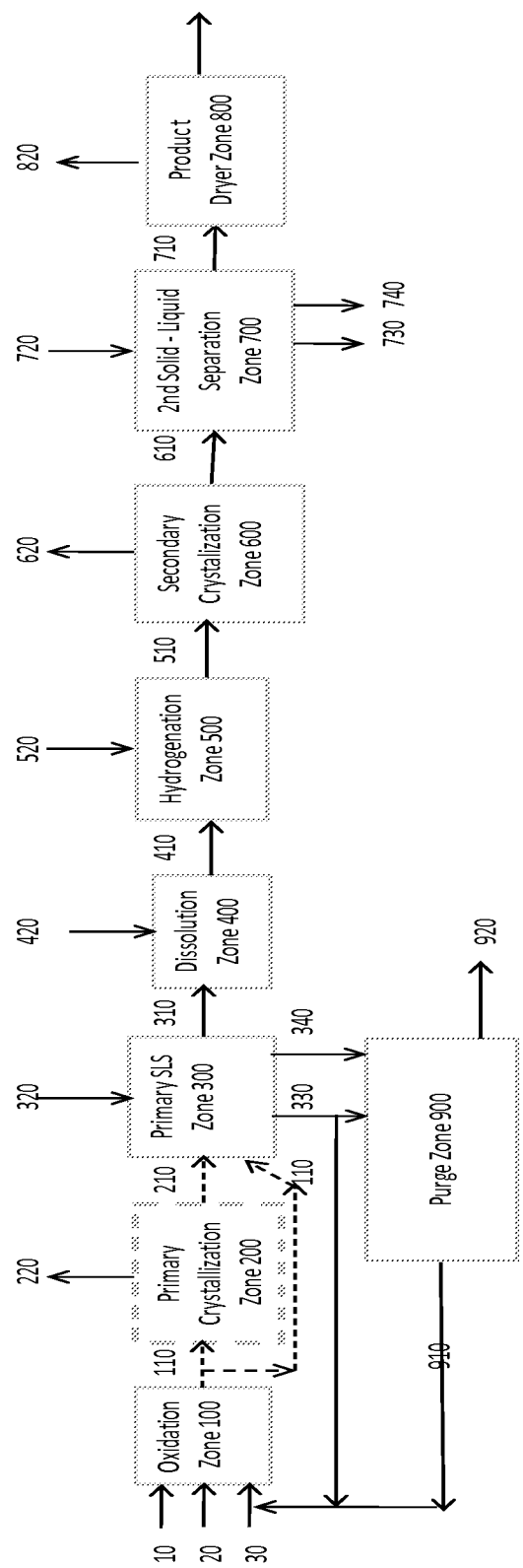
FIG. 1 is a flow diagram of the process for making a concentrated hFDCA composition.

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/− 19° F.), and a narrow numerical range of 53° F. to 71° F. (62° F.+/− 9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively All amounts and ppm values are by weight unless otherwise specified. All amounts by weight are based on the weight of the whole composition stream containing the ingredient in question rather than a part of that composition or a different stream altogether, unless otherwise noted.

There is provided a crude FDCA (cFDCA) composition comprising furan 2,5-dicarboxylic acid (FDCA) solids, 5-formyl furan-2-carboxyic acid (FFCA), and a oxidation solvent composition. This composition may be provided in a variety of ways. One technique is described as follows.

As shown in FIG. 1, an oxidizable composition is fed in stream 10 to an oxidation zone 100, where the oxidizable composition contains a compound having a furan moiety. The furan moiety can be represented by the structure:

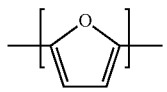

The compounds having a furan moiety are such that, upon oxidation, form carboxylic acid functional groups on the compound. Examples of compounds having furan moieties include 5-(hydroxymethyl)furfural (5-HMF), and derivatives of 5-HMF. Such derivatives include esters of 5-HMF, such as those represented by the formula 5-R(CO)OCH$_2$-furfural where R=alkyl, cycloalkyl and aryl groups having from 1 to 8 carbon atoms, or 1-4 carbon atoms or 1-2 carbon atoms; ethers of 5-HMF represented by the formula 5-R'OCH$_2$-furfural, where R'=alkyl, cycloalkyl and aryl having from 1 to 8 carbon atoms, or 1-4 carbon atoms or 1-2 carbon atoms); 5-alkyl furfurals represented by the formula 5-R"-furfural, where R"=alkyl, cycloalkyl and aryl having from 1 to 8 carbon atoms, or 1-4 carbon atoms or 1-2 carbon atoms). Thus the oxidizable composition can contain mixtures of 5-HMF and 5-HMF esters; 5-HMF and 5-HMF ethers; 5-HMF and 5-alkyl furfurals, or mixtures of 5-HMF and its esters, ethers, and alkyl derivatives.

The oxidizable composition, in addition to 5-(hydroxymethyl)furfural (5-HMF) or an of its derivatives, may also contain 5-(acetoxymethyl)furfural (5-AMF) and 5-(ethoxymethyl)furfural (5-EMF).

Specific examples of 5-HMF derivatives include those having the following structures:

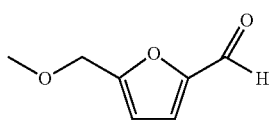
5-methoxymethylfurfural

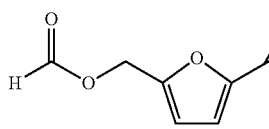
5-formoxymethylfurfural

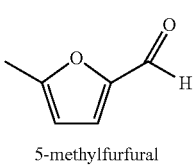
5-methylfurfural

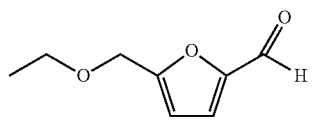
5-ethoxymethylfurfural

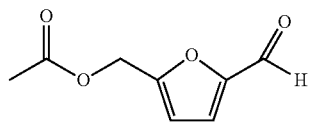
5-acetoxymethylfurfural

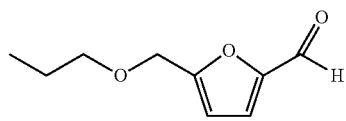
5-propoxymethylfurfural

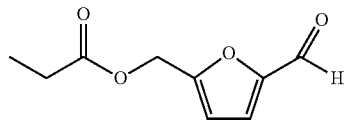
5-propionoxymethylfurfural

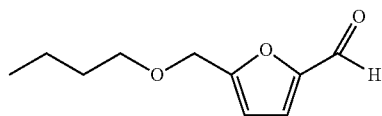
5-butoxymethylfurfural

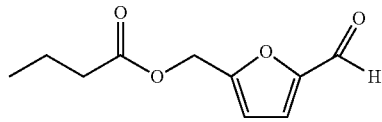
5-butyroxymethylfurfural

An oxidizable composition is fed to a primary oxidation zone and reacted in the presence of a oxidation solvent composition, a catalyst system, and a gas comprising oxygen, to generate a crude dicarboxylic acid stream comprising furan-2,5-dicarboxylic acid (FDCA).

For example, the oxidizable composition containing 5-HMF, or its derivatives, or combinations thereof, are oxidized with $O_2$ in a multi-step reaction to form FDCA with 5-formyl furan-2-carboxylic acid (FFCA) as a key intermediate, represented by the following sequence:

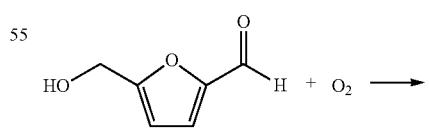
5-HMF

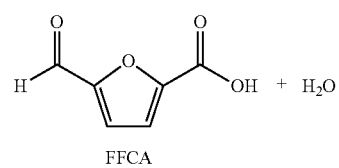
FFCA

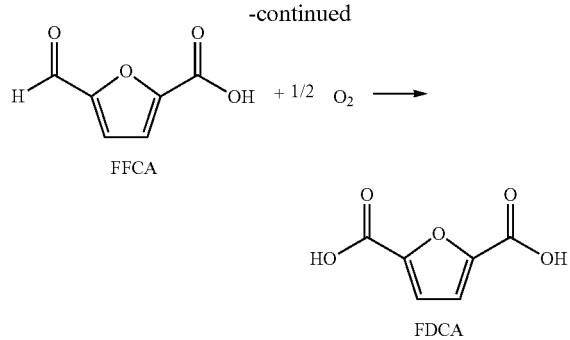

If desired, the oxygen gas stream 20 comprising oxygen, an oxidation solvent composition stream 30, and the oxidizable stream 10 can be fed to a primary oxidation zone 100 as separate streams. Or, an oxygen stream comprising oxygen as one stream and an oxidizable stream comprising oxidation solvent composition, catalyst, and oxidizable compounds as a second stream can be fed to the primary oxidation zone. Accordingly, the oxidation solvent composition, oxygen gas comprising oxygen, catalyst system, and oxidizable compounds can be fed to the primary oxidization zone as separate and individual streams or combined in any combination prior to entering the primary oxidization zone wherein these feed streams may enter at a single location or in multiple locations into the primary oxidizer zone.

The catalyst can be a homogenous catalyst soluble in the oxidation solvent composition or a heterogeneous catalyst. The catalyst composition is desirably soluble in the oxidation solvent composition under reaction conditions, or it is soluble in the reactants fed to the oxidation zone. Preferably, the catalyst composition is soluble in the oxidation solvent composition at 40° C. and 1 atm, and is soluble in the oxidation solvent composition under the reaction conditions.

Suitable catalysts components comprise at least one selected from, but are not limited to, cobalt, bromine and manganese compounds. Preferably a homogeneous catalyst system is selected. The preferred catalyst system comprises cobalt, manganese and bromine.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate. The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

The amount of bromine atoms desirably ranges from at least 300 ppm, or at least 2000 ppm, or at least 2500 ppm, or at least 3000 ppm, or at least 3500 ppm, or at least 3750, ppm and up to 4500 ppm, or up to 4000 ppm, based on the weight of the liquid in the reaction medium of the primary oxidation zone. Bromine present in the amount of 2500 ppm to 4000 ppm, or 3000 ppm to 4000 ppm are especially desirable to promote high yield.

The amount of cobalt atoms can range from at least 500 ppm, or at least 1500 ppm, or at least 2000 ppm, or at least 2500 ppm, or at least 3000 ppm, and up to 6000 ppm, or up to 5500 ppm, or up to 5000 ppm, based on the weight of the liquid in the reaction medium of the primary oxidation zone. Cobalt present in an amount of 2000 to 6000 ppm, or 2000 to 5000 ppm is especially desirable to promote high yield.

The amount of manganese atoms can range from 2 ppm, or at least 10 ppm, or at least 30 ppm, or at least 50 ppm, or at least 70 ppm, or at least 100 ppm, and in each case up to 600 ppm, or up to 500 ppm or up to 400 ppm, or up to 350 ppm, or up to 300 ppm, or up to 250 ppm, based on the weight of the liquid in the reaction medium of the primary oxidation zone. Manganese present in an amount ranging from 30 ppm to 400 ppm, or 70 ppm to 350 ppm, or 100 ppm to 350 ppm are especially desirable to promote high yield.

The weight ratio of cobalt atoms to manganese atoms in the reaction mixture can be from 1:1 to 400:1, or 10:1 to about 400:1. A catalyst system with improved Co:Mn ratio can lead to high yield of FDCA. To increase the yield of FDCA, when the oxidizable composition fed to the oxidation reactor comprises 5-HMF, then the cobalt to manganese weight ratio is at least 10:1, or at least 15:1, or at least 20:1, or at least 25:1, or at least 30:1, or at least 40:1 or at least 50:1, or at least 60:1, and in each case up to 400:1. However, in the case where the oxidizable composition comprises esters of 5-HMF, ethers of 5-HMF, or 5-alkyl furfurals, or mixtures of any of these compounds together or with 5-HMF, the cobalt to manganese weight ratio can be lowered while still obtaining high yield of FDCA, such as a weight ratio of Co:Mn of at least 1:1, or at least 2:1, or at least 5:1, or at least 9:1, or at least 10:1, or at least 15:1, or at least 20:1, or at least 25:1, or at least 30:1, or at least 40:1, or at least 50:1, or at least 60:1 and in each case up to 400:1.

The weight ratio of cobalt atoms to bromine atoms is desirably at least 0.7:1, or at least 0.8:1, or at least 0.9:1, or at least 1:1, or at least 1.05:1, or at least 1.2:1, or at least 1.5:1, or at least 1.8:1, or at least 2:1, or at least 2.2:1, or at least 2.4:1, or at least 2.6:1, or at least 2.8:1, and in each case up to 3.5, or up to 3.0, or up to 2.8.

The weight ratio of bromine atoms to manganese atoms is from about 2:1 to 500:1.

Desirably, the weight ratio of cobalt to manganese is from 10:1 to 400:1, and the weight ratio of cobalt to bromine atoms ranges from 0.7:1 to 3.5:1. Such a catalyst system with improved Co:Mn and Co:Br ratio can lead to high yield of FDCA (minimum of 90%), decrease in the formation of impurities (measured by b*) causing color in the downstream polymerization process while keeping the amount of CO and $CO_2$ (carbon burn) in the off-gas at a minimum.

Desirably, the amount of bromine present is at least 1000 ppm and up to 3500 ppm, and the weight ratio of bromine to manganese is from 2:1 to 500:1. This combination has the advantage of high yield and low carbon burn.

Desirably, the amount of bromine present is at least 1000 ppm and up to 3000 ppm, and the amount of cobalt present is at least 1000 ppm and up to 3000 ppm, and the weight ratio of cobalt to manganese is from 10:1 to 100:1. This combination has the advantage of high yield and low carbon burn.

Suitable oxidation solvent compositions include aliphatic oxidation solvent compositions. In an embodiment of the invention, the oxidation solvent compositions are aliphatic carboxylic acids which include, but are not limited to, $O_2$ to $O_6$ monocarboxylic acids, e.g., acetic acid, propionic acid, n-butyric acid, isobutyric acid, n-valeric acid, trimethylacetic acid, caprioic acid, and mixtures thereof.

The most common oxidation solvent composition used for the oxidation is an -aqueous acetic acid solution, typically having an acetic acid concentration of 80 to 99 wt. % before adding it to the oxidation zone. In especially preferred embodiments, the oxidation solvent composition as added comprises a mixture of water and acetic acid which has a water content of 0% to about 15% by weight. Additionally, a portion of the oxidation solvent composition feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 0 to 15% water.

The oxidizing gas stream comprises oxygen. Examples include, but are not limited to, air and purified oxygen. The amount of oxygen in the primary oxidation zone ranges from about 5 mole % to 45 mole %, 5 mole to 60 mole %, 5 mole % to 80 mole %.

The temperature of the reaction mixture in the primary oxidation zone can vary from about 100° C. to about 220° C. The temperature of the reaction mixture in the primary oxidation zone is at least 100° C., or at least 105° C., or at least 110° C., or at least 115° C., or at least 120° C., or at least 125° C., or at least 130° C., or at least 135° C., or at least 140° C., or at least 145° C., or at least 150° C., or at least 155° C., or at least 160° C., and can be as high as 220° C., or up to 210° C., or up to 200° C., or up to 195° C., or up to 190° C., or up to 180° C., or up to 175° C., or up to 170° C., or up to 165° C., or up to 160° C., or up to 155° C., or up to 150° C., or up to 145° C., or up to 140° C., or up to 135° C., or up to 130° C. In other embodiments, the temperate ranges from 105° C. to 180° C., or from 105° C. to 175° C., or from 105° C. to 170° C., or from 105° C. to 165° C., or from 105° C. to 160° C., or from 105° C. to 155° C., or from 105° C. to 150° C., or from 110° C. to 180° C., or from 110° C. to 175° C., or from 110° C. to 170° C., or from 110° C. to 165° C., or from 110° C. to 160° C., or from 110° C. to 155° C., or from 110° C. to 150° C., or from 110° C. to 145° C., or from 115° C. to 180° C., or from 115° C. to 175° C., or from 115° C. to 170° C., or from 115° C. to 165° C., or from 115° C. to 160° C., or from 115° C. to 155° C., or from 110° C. to 150° C., or from 115° C. to 145° C., or from 120° C. to 180° C., or from 120° C. to 175° C., or from 120° C. to 170° C., or from 120° C. to 165° C., or from 120° C. to 160° C., or from 120° C. to 155° C., or from 120° C. to 150° C., or from 120° C. to 145° C., or from 125° C. to 180° C., or from 125° C. to 175° C., or from 125° C. to 170° C., or from 125° C. to 165° C., or from 125° C. to 160° C., or from 125° C. to 155° C., or from 125° C. to 150° C., or from 125° C. to 145° C., or from 130° C. to 180° C., or from 130° C. to 175° C., or from 130° C. to 170° C., or from 130° C. to 165° C., or from 130° C. to 160° C., or from 130° C. to 155° C., or from 130° C. to 150° C., or from 130° C. to 145° C., or from 135° C. to 180° C., or from 135° C. to 175° C., or from 135° C. to 170° C., or from 135° C. to 165° C., or from 135° C. to 160° C., or from 135° C. to 155° C., or from 135° C. to 150° C., or from 135° C. to 145° C., or from 140° C. to 180° C., or from 140° C. to 175° C., or from 140° C. to 170° C., or from 140° C. to 170° C., or from 140° C. to 165° C., or from 140° C. to 160° C., or from 140° C. to 155° C., or from 140° C. to 150° C., or from 140° C. to 145° C., or from 145° C. to 180° C., or from 145° C. to 175° C., or from 145° C. to 170° C., or from 145° C. to 170° C., or from 145° C. to 165° C., or from 145° C. to 160° C., or from 145° C. to 155° C., or from 145° C. to 150° C., or from 150° C. to 180° C., or from 150° C. to 175° C., or from 150° C. to 170° C., or from 150° C. to 165° C., or from 150° C. to 160° C., or from 150° C. to 155° C., or from 155° C. to 180° C., or from 155° C. to 175° C., or from 155° C. to 170° C., or from 155° C. to 165° C., or from 155° C. to 160° C., or from 160° C. to 180° C., or from 160° C. to 175° C., or from 160° C. to 170° C., or from 160° C. to 165° C., or from 165° C. to 180° C., or from 165° C. to 175° C., or from 165° C. to 170° C., or from 165° C. to 180° C., or from 165° C. to 175° C., or from 165° C. to 170° C., or from 170° C. to 180° C., or from 170° C. to 175° C., or from 175° C. to 180° C.

To minimize carbon burn, it is desired that the temperature of the reaction mixture is not greater than 165° C., or not greater than 160° C. The contents of the oxidizer off gas comprise COx, wherein x is 1 or 2, and the amount of COx in the oxidizer off gas is less than 0.05 moles of COx per mole of the total oxidizable feed to the reaction medium, or no more than 4 moles of COx per mole of the total oxidizable feed to the reaction medium, or no more than 6 moles of COx per mole of the total oxidizable feed to the reaction medium. The carbon burn as determined by the COx generation rate can be calculated as follows: (moles of CO+ moles of CO2)/moles of oxidizable feed. The low carbon burn generation rate is achievable by the combination of low reaction temperature, and the molar weight ratios of the catalyst components as described above.

The oxidation reaction can be conducted under a pressure ranging from 40 psia to 300 psia. A bubble column is desirably operated under a pressure ranging from 40 psia to 150 psia. In a stirred tank vessel, the pressure is desirably set to 100 psia to 300 psia.

Oxidizer off gas stream containing COx (CO and $CO_2$), water, nitrogen, and vaporized oxidation solvent composition, is routed to the oxidizer off gas treatment zone to generate an inert gas stream, liquid stream comprising water, and a recovered oxidation solvent composition stream comprising condensed oxidation solvent composition. In one embodiment, the oxidizer off gas stream can be fed to directly, or indirectly after separating condensables such as oxidation solvent composition from non-condensables such as COx and nitrogen in a separation column (e.g. distillation column with 10-200 trays), to an energy recovery device such as a turbo-expander to drive an electric generator. Alternatively or in addition, the oxidizer off gas stream can be fed to a steam generator before or after the separation column to generate steam, and if desired, may then be fed to a turbo-expander and pre-heated prior to entry in the expander if necessary to ensure that the off gas does not condense in the turbo-expander.

The oxidation can be conducted in a continuous stirred tank reactor or in a bubble column reactor.

The FDCA formed by the oxidation reaction desirably precipitates out of the reaction mixture. The reaction mixture comprises the oxidizable composition, oxidation solvent composition, and catalyst if a homogeneous catalyst is used, otherwise it comprises the oxidizable composition and oxidation solvent composition.

The product of the oxidation reaction is a crude dicarboxylic acid stream ("cFDCA") comprising solids, said solids comprising FDCA; an oxidation solvent composition; and the intermediate product 5-formyl furan-2-carboxylic acid ("FFCA"), and oxidation solvent. The above description is illustrative of one of the means by which one may provide for a cFDCA composition comprising furan 2,5-dicarboxylic acid (FDCA) solids, 5-formyl furan-2-carboxylic acid (FFCA), and a liquid oxidation solvent composition. The cFDCA may also contain some amount of FDCA dissolved in the oxidation solvent composition and if used, some of the homogeneous catalyst system. The cFDCA is colored as a result of the production of color by-products. The presence color bodies can be detected by measuring the b* of the cFDCA composition. The cFDCA composition may also contain mono-carboxylic acid FFCA which is not desirable because it acts to terminate chain growth in a polymerization reaction using an FDCA composition as a reactant.

The cFDCA composition desirably comprises:
a) solids in an amount of at least 5 wt. %, or at least 10 wt %, or at least 15 wt. %, or at least 20 wt. %, or at least 25 wt. %, or at least 28 wt. %, or at least 30 wt. %, or at least 32 wt. %, or at least 35 wt. %, or at least 37 wt. %, or at least 40 wt. %, based on the weight of the cFDCA composition. While there is no upper limit, as a practice the amount will not exceed 60 wt. %, or no greater than 55 wt. %, or no greater than 50 wt. %, or no greater than 45 wt. %., or not greater than 43 wt. %, or not greater than 40 wt %, or not greater than 39 wt %, based on the weight of the cFDCA composition;
b) of the solids in the crude dicarboxylic acid stream, it is desirable that at least 70 wt. %, or at least 80 wt. %, or at least 85 wt. %, or at least 90 wt. %, or at least 95 wt. %, or at least 96 wt. %, or at least 97 wt. %, or at least 98 wt. %, or at least 99 wt. % of the solids in each case is FDCA based on the weight of the solids;
c) at least 0.1 wt. % FFCA, or at least 0.2 wt. % FFCA, or at least 0.3 wt. % FFCA, or at least 0.35 wt. % FFCA, or at least 0.4 wt. % FFCA, and can contain large amounts of FFCA, such as up to 5 wt. %, or up to 4 wt. %, or up to 3 wt %, or up to 2 wt. %, based on the weight of the cFDCA composition.

Optionally, in addition to FFCA, other by-products can also be present in the cFDCA composition such as color bodies. Color bodies can be formed from impurities present in the oxidizable composition, e.g. 5-HMF composition fed into the oxidation zone, or degradation products produced in the course of the oxidation of the 5-HMF composition. Other by-products present in the cFDCA composition can include, for example, compounds such as 2,5-diformylfuran, levulinic acid, succinic acid, acetoxyacetic acid, 5-(ethoxycarbonyl)furan-2-carboxylic acid ("EFCA"), and their oxidation derivatives. 2,5 diformylfuran can be present, if at all, in an amount of 0 wt % to about 0.2 wt %; levulinic acid in an amount ranging from 0 wt % to 1 wt. % or up to 0.5 wt %; succinic acid in an amount ranging from 0 wt % to 1 wt. %, or up to 0.5 wt %; EFCA in an amount of greater than 0, or at least 0.05 wt %, or at least 0.1 wt %, or at least 0.5 wt % and in each case up to about 4 wt %, or up to about 3.5 wt %, or up to 3 wt. %, or up to 2.5 wt %, or up to 2 wt. %; acetoxyacetic acid in an amount ranging from 0 wt % to 0.5 wt %, and a cumulative amount of the by-products (includingFFCA) can be present in an amount ranging from greater than 0 wt. %, or at least 0.1 wt. %, or at least 0.5 wt. %, or at least 1 wt. %, or at least 2 wt. %, and up to 30 wt. %, or up to 20 wt. %, or up to 15 wt. %, or up to 10 wt. %, or up to 5 wt. %, or up to 3 wt. %, or up to 2 wt. %, or up to 1 wt. %., in each case based on the weight of cFDCA composition.

Because some of the by-products present in the cFDCA, the cFDCA composition may be color bodies and/or the cFDCA composition may contain FFCA which is a chain terminating compound, it is desirable to subject the cFDCA composition to a process for the production of a low color purified FDCA composition. The cFDCA composition may have a high b*. While the b* value is not limited, the cFDCA composition will typically have a b* of more than 3, or more than 4, or more than 5, or more than 6, or more than 7, or at least 10, or at least 15, or at least 20, or at least 25, or at least 30, or at least 35, or at least 35. While there is not upper limit, generally the b* will not exceed 90, or not exceed 80. However, it is desirable to lower the b* of cFDCA compositions that have lower b* value, such as up to 70, or up to 60, or up to 50, or up to 30, or up to 20, or up to 15, or up to 10, or up to 8, or up to 6. Even with a b* of at least 1 and up to 5, or up to 4, it is desirable to purify the cFDCA composition to lower the b* color and/or reduce the amount of FFCA. Although the b* may not be an important consideration for a particular application, some applications require chain propagation and therefore it is desirable to purify the cFDCA composition to reduce the amount of FFCA present.

While the amount of FFCA present in the cFDCA composition is not limited, the process of the invention is effective to reduce the amount of FFCA present in the cFDCA composition, relative to the amount of FFCA in the purified FDCA composition, in each case by weight, by a factor of at least 2×, or at least 10×, or at least 100×, or at least 200×, or at least 300×, or at least 350×, or at least 400×, or at least 500×, or at least 750×, or at least 900×, or at least 1000×, or at least 1500×, calculated as:

$x$ reduction=ppmw FFCA in cFDCA divided by ppmw FFCA in purified FDCA composition (where FFCA detected in the purified FDCA composition at a value below 1 ppmw, or undetectable by virtue of its absence or below the detection limit of an analytical instrument, is, for purposes of this calculation, taken as a value of 1 ppm).

The yield of FDCA in the cFDCA composition, on a solids basis, is at least 60%, or at least 65%, or at least 70%, or at least 72%, or at least 74%, or at least 76%, or at least 78%, or at least 80%, or at least 81%, or at least 82%, or at least 83%, or at least 84%, or at least 85%, or at least 86%, or at least 87%, or at least 88%, or at least 89%, or at least 90%., or at least 91%, or at least 92%, or at least 94%, or at least 95%, and up to 99%, or up to 98%, or up to 97%, or up to 96%, or up to 95%, or up to 94%, or up to 93%, or up to 92%, or up to 91%, or up to 90%, or up to 89%. For example, the yield can range from 70% up to 99%, or 74% up to 98%, or 78% up to 98%, or 80% up to 98%, or 84% up to 98%, or 86% up to 98%, or 88% up to 98%, or 90% up to 98%, or 91% up to 98%, or 92% up to 98%, or 94% up to 98%, or 95% up to 99%.

Yield is defined as mass of FDCA obtained divided by the theoretical amount of FDCA that should be produced based on the amount of raw material use. For example, if one mole or 126.11 grams of 5-HMF are oxidized, it would theoretically generate one mole or 156.09 grams of FDCA. If for example, the actual amount of FDCA formed is only 150 grams, the yield for this reaction is calculated to be=(150/156.09) times 100, which equals a yield of 96%. The same calculation applies for oxidation reaction conducted using 5-HMF derivatives or mixed feeds.

In a second step, at least a portion of the oxidation solvent is separated from the FDCA solids in the cFDCA composition to generate a concentrated cFDCA composition comprising FDCA solids and enriched in the concentration of solids relative to the concentration of solids in the cFDCA composition fed to the solid-liquid separation zone. This can be accomplished by any means known in the art for separating solids from liquids. One means for separation is a solid liquid separation zone 300. In the solid-liquid separation zone 300, at least a portion of the oxidation solvent composition is separated from FDCA solids, the FDCA solids are optionally washed, and then discharged as a concentrated FDCA composition 310.

The feed to the solid-liquid separation zone 300 contains FDCA solids and oxidation solvent. Of the liquid phase, the oxidation solvent desirably comprises at least 70 wt. %, or at least 80 wt. %, or at least 90 wt. %, or at least 95 wt. %, or at least 99 wt. %, or even up to 99.5 wt. % of the liquid based on the weight of the liquid phase of the feed to the solid liquid separator, excluding the amount due to the presence of water.

The feed to the solid-liquid separation zone 300 contains FDCA solids and oxidation solvent. The cFDCA composition desirably contains at least 40%, or at least 50 wt. %, or at least 70 wt. %, or at least 80 wt. %, or at least 90 wt. %, and up to about 95 wt. % liquid based on the weight of the cFDCA composition.

The feed to the first solid liquid separation zone can be the cFDCA composition stream 110 discharged from the oxidation zone 100. Alternatively, an optional crude crystallization zone 200 may be used to receive a feed of the cFDCA to obtain a crystallized cFDCA composition which is discharged from the crude crystallization zone 200 as a feed stream 210. If desired, the solid liquid separation zone 300 can receive from zero to 100% by weight of stream 210 which is a crystallized cFDCA composition, or from 0 to 100% by weight stream 110 which is the cFDCA composition, or a combination of cFDCA stream 110 and crystallized cFDCA composition stream 210 in any weight ratio ranging from 100:0 to 0:100 respectively.

In the solid-liquid separation zone, FDCA solids are separated from at least a portion of the oxidation solvent composition. The first solid liquid separation zone may contain a zone in which at least a portion of the oxidation solvent is separated from FDCA solids to generate a cake comprising FDCA solids is generated (cake forming zone), a mother liquor comprising oxidation solvent is generated, and the cake is washed with at least one wash composition. The first solid-liquid separation zone may also contain a drying zone. Each one of these zones may be contained in a single solid-liquid separation device. One or multiple solid-liquid separation devices may be employed. The solid-liquid separation zone desirably contains at least one solid-liquid separation device capable of separating solids and liquids, and washing the solids with a wash composition stream 320. The solid-liquid separation can be accomplished by means of filtration. The filtration can be positive displacement or vacuum filtration. Washing can also be a positive displacement washing, reflux, or counter-current washing techniques. The drying, if employed, can be accomplished by blowing a gas on the filtrate cake.

Equipment suitable for the solid liquid separation zone can typically be comprised of, but not limited to, the following types of devices: centrifuges of all types including but not limited to decanter and disc stack centrifuges, cross flow filters, solid bowl centrifuges, cyclone, rotary drum filter, belt filter desirably a horizontal belt filter with or without but desirably with at least one washing zone and can optionally contain countercurrent washing, pressure leaf filter, candle filter, a rotary vacuum drum filter with or without but desirably with at least one washing zone and can optionally contain countercurrent washing, or a rotary pressure drum filter with or without but desirably with washing and can optionally contain countercurrent washing. The solid-liquid separator may be operated in continuous or batch mode, although it will be appreciated that for commercial processes, the continuous mode is preferred. A suitable pressure filter which can be employed as the solid/liquid separator is a BHS-FEST™, available from BHS-WERK, Sonthofen, D-8972, Sonthofen, West Germany.

The temperature of the wash solvent can range from 20° C. to 180° C., or 40° C. and 150° C., or 50° C. to 140° C., or 70° C. to 140° C., or 80° C. to 140° C., or in each case up to 130° C. The particular wash temperature desirably does not exceed a temperature at which a substantial amount of the filtrate cake dissolves away into the wash solvent liquor. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

Within the solid liquid separation zone, and after separation of the liquid from the solids or simultaneous with the separation, one or more washes may be implemented in the solid-liquid separation zone. One or more of the washes, desirably at least the final wash, may contain at least 80 wt. %, or at least 90 wt. %, or at least 95 wt. %, or 100 wt. % water. For example, the solid liquid separation zone may contain at least two wash zones, a first wash zone in which a wash composition containing an organic solvent having at least two carbon atoms (e.g. acetic acid or the same compound as the oxidation solvent contained in the cFDCA composition) is contacted with the FDCA solids to wash away impurities from the surface of the FDCA solids, and a second wash zone in which a wash composition containing at least 80 wt. % water contacts the FDCA solids to wash away at least a portion of the organic solvent. If desired, two or more wash zones may be employed. Further, each of the wash zones may become progressively and sequentially richer in concentration of water. The advantage of employing a final wash containing at least 80 wt. % water is that water can be the same solvent as used in the dissolution zone 400. The discharge can be a water wet cake stream 310. Another advantage is that one can avoid drying of the FDCA solids containing water prior to feeding the water wet cake to the dissolution zone, thereby saving energy and capital costs.

However, if one desires to produce stream 310 in a dried powder form, then at least the final wash solvent composition desirably contains solvents that have lower heats of vaporization than water to save on energy costs to vaporize the solvent in the dryer.

The principle of operating a solid liquid separation zone is illustrated with reference to a rotary drum filter. In a rotary pressure drum filter, a stream of cFDCA composition 110, or crystallized cFDCA composition stream 210, is continuously fed to the inlet of a housing containing a drum within the annulus between the drum outer surface and the housing. The annulus is sealed and under pressure. The feed is introduced into the inlet of the housing at one end, into the annulus, and contacts the rotating drum surface that is divided into filter cells that receive the FDCA feed composition and allow the liquid to pass through the filter media while forming a cake on the drum surface. The filtrate cake of FDCA solids formed on each filter cell can be independently processed in discrete zones. Each of the zones can be operated under different pressures. In a rotary vacuum drum filter, the feed of FDCA is introduced into a bath within an annulus between a housing and the drum, and in this case, a vacuum is pulled through the filter cloth to draw liquid from the bath through the filter media, thereby forming a cake on the drum surface as the drum rotates radially through the bath of feed material.

Once the cake is formed on the drum in the cake forming zone, it can continue to be processed in discrete zones throughout its rotation, and with the pressure filter, each under independently controlled pressure which can be the same or variable. Upon exiting the zone for cake formation, the drum continues its rotation into a wash zone where the cake is subjected to a flooded positive displacement wash for pressure filtration or a spray in vacuum drum filtration, or other suitable contact means, of a wash solvent. One wash zone may introduce acetic acid, and a second wash zone may introduce water onto the surface of the cake. In the pressure filter, the wash zone can consist of one or more chambers that are flooded with wash solvent pulled through the cake under a vacuum. If desired, the multiple wash cells in pressure filtration can form a counter-current wash of the cake.

Upon exiting the wash zone, the filtrate cake on the outer drum surface can optionally be dewatered (not implying that the solvent is water) by blowing a flow of a gas, such as air or nitrogen, across and/or through the cake. The blown gas can be at ambient temperature or elevated temperature. The degree of dewatering the cake is influenced by the gas flow, gas temperature, cake depth, vapor pressure of the solvent in the cake, cake depth and residence time.

As the drum continues its rotation, the wet cake is then discharged from the drum surface by any suitable means, optionally with the assistance of a blown gas through jets. The cake can be discharged by feeding the cake on the outer drum surface onto the edge of a blade to scrape and flake the cake from drum surface. Discharge of the cake can be assisted by spraying a jet of water onto or through the back or front side of the filter media to dislodge the filtrate from the drum surface. This assisted cake discharge has the advantage of more readily dislodging the cake from drum surface while using the jetted water as the liquid medium into which the FDCA solids will eventually be dissolved in the dissolution zone 400.

After discharging the cake from the outer drum surface, the filter media is desirably washed clean or conditioned before the drum rotates into the cake formation zone. The filter media can be washed with a rinse of water, gas, or the same solvent as in the cFDCA composition using jets or sprays. The assisted discharge of the cake from the outer drum surface can serve the dual function of assisting discharge while washing the filter media.

This illustration is given as two examples of a solid-liquid separation device. Any other suitable solid-liquid separation devices can be used, and each zone can be split into different devices if desired.

With a solid-liquid separation device that has a wash zone, a mother liquor stream and a wash liquor stream are generated and discharged from the solid-liquid separation device and the wash zones. Mother liquor stream 330 is generated upon separation of at least a portion of the oxidation solvent from the FDCA solids. In a rotary drum filter device, this mother liquor is generated in the cake formation zone. A wash liquor stream 340 is generated by contacting the wash composition in the wash zone with the FDCA solids (e.g. cake on the outer drum surface or on a belt surface) desirably after generation of the mother liquor stream 330. A portion of the mother liquor stream 330 and optionally a portion of at least the first wash liquor stream 340 can be routed to a purge zone 900 to recover at least a portion of the catalyst and oxidation solvent for recycle to the oxidation zone, while the remaining portion can be recycled directly back to the oxidation zone 100. In one embodiment, from 5% to 100% by weight of the displaced mother liquor stream 330 is routed to a purge zone 900 wherein a portion of the impurities present in mother liquor stream 330 are isolated and exit the process as purge stream 920, wherein a portion is 5% by weight or greater. Recovered solvent stream 910 comprises solvent and catalyst isolated from stream 330 and is recycled to the oxidation zone 100. The recovered solvent stream 910 contains greater than 30% of the catalyst that entered the purge zone 900 in stream 330. The stream 910 recycled to the oxidation zone 100 may contain greater than 50 weight %, or greater than 70 weight %, or greater than 90 weight % of the catalyst that enters the purge zone 900 in stream 330 on a continuous or batch basis.

As mentioned above, instead of feeding the cFDCA composition to a solid-liquid separation zone, the cFDCA zone can optionally and desirably be fed into a crude crystallization zone 200 before the solid-liquid separation zone. Feeding the cFDCA composition to a crude crystallization zone 200 has the advantage of generating a larger amount of FDCA solids by transforming at least a portion of FDCA in the liquid phase of the cFDCA composition into a solid phase, and desirably also increasing the crystal size of the solids. It also has the advantage of lowering the temperature of the cFDCA stream so that the solid-liquid separator is not subjected to the extreme high temperatures of the cFDCA composition exiting the oxidation zone.

The cFDCA composition 110 can be crystallized in a crude crystallization zone 200 to form a crystallized cFDCA slurry stream 210. Generally, the crude crystallization zone 200 contains at least one crystallization device. The crystallization device can be a flash vessel, a vessel equipped with vacuum forming means or a heat exchanger to cool, or both. The off-gas from the crystallizer is a vapor composition stream 220 that can be condensed in at least one condenser and returned to the crystallization zone. Optionally, the liquid from the condenser or vapor product from the crude crystallization zone can be recycled to the oxidation zone 100, or it can be withdrawn or sent to an energy recovery device. In addition, the vapor composition removed via line 220 can be routed to a recovery system where the oxidation solvent is removed and remaining VOCs may be treated, for example by incineration in a catalytic oxidation unit.

The crystallized cFDCA stream 210 exiting the crystallization zone 200 is at a temperature that is at least 15° C., or at least 20° C., or at least 30° C., or at least 40° C., or at least 50° C., or at least 60° C., or at least 70° C., or at least 80° C. less than the temperature of the cFDCA composition fed to the crystallization zone. Desirably, the temperature of at least one of the crystallization vessels within the crude crystallization zone 200 is operated at a temperature within a range of 40° C. to 160° C., or 50° C. to 150° C., or 60° C. to 140° C.

Depending upon the type of solid-liquid separation device used, it is desirable to configure the crude crystallization zone 200 to reduce the temperature of the cFDCA entering the crystallization zone 200 sufficient so that the solvent does not significantly flash in cake forming zone of the solid-liquid separation device, especially in vacuum filtration.

One method for cooling the cFDCA composition stream 110 can be accomplished by operating the crude crystallization zone 200 under a pressure that is lower than pressure of the cFDCA composition feeding the crystallization zone. Means for lowering the pressure include allowing the cFDCA stream to be fed into a flash vessel operated at or above ambient pressure or at or above 1 atm., a crystallization vessel that is operated under a vacuum of less than 1 atm, cooling coils such as would be found in a heat exchanger, or a combination of these means. Desirably, at least one of the crystallization vessels is operated under a vacuum of less than 1 atm. while simultaneously flashing at least a portion of the cFDCA fed to the vessel, optionally also operating as a mechanically stirred tank.

It is also desirable, if more than one crystallization vessel is employed in series, for the pressure within a downstream crystallization vessel to be lower than the pressure of at least one crystallization vessel upstream in the series, and even more desirable is that the pressure within each crystallization vessel is lower with each downstream successive vessel in the series. The pressure reduction from the feed inlet to the discharge within at least one crystallization vessel, and desirably the pressure differential of at least two vessels, and more desirably the pressure differential of each successive crystallization vessel in the series (comparing the operating pressure of one vessel to another vessel and taking the difference), can be at least 10 Torr, or at least 20 Torr, or at least 30 Torr, or at least 50 Torr, or at least 100 Torr. One or more of the crystallizer vessels can be a mechanically stirred tank.

Taking as an example, 3 vessels can be operated in series within the crystallization zone, the first vessel in the crystallization zone can be a flash tank operated at or greater than ambient pressure, the second vessel can be a flash evaporation crystallizer vessel operated under a vacuum of 750 Torr absolute or less, or 600 Torr absolute or less, or 400 Torr absolute or less with a feed inlet above the liquid level within the vessel that introduces the cFDCA feed into the vessel, desirably across a pressure drop (such as a valve or pipe constriction) to flash the oxidation solvent, and the third vessel can be a crystallizer vessel, optionally operated with flash evaporation, under a vacuum of less than 750 Torr absolute, or at a pressure that is less than the second vessel by 10 Torr or greater, or 100 Torr or greater.

There exists a temperature drop from one crystallization vessel to the next succeeding crystallization vessel of at least two adjacent vessels. Desirably, the temperature drop between at least two adjacent crude crystallization vessels in the series, and desirably of each adjacent crude crystallization vessel (which includes a flash tank) in a series, is desirably at least 10° C., or at least 20° C., or at least 30° C. For example in a series of 4 crystallization vessels, the second in the series will be operated at a temperature that is at least 10° C. cooler than the first in the series, and the third in the series will be operated at a temperature that is at least 10° C. cooler than the second, and the fourth will be operated at a temperature that is at least 10° C. cooler than the third in the series. Desirably, the first in the series cools the cFDCA feed by at least 10° C., although if the first vessel in the series is a flash evaporation tank, the amount of cooling in this tank may be less than 10° C.

Any other method of cooling may be employed in addition to or in place of evaporative cooling and/or cooling tubes, but in any event, there is desirably a temperature drop across the cFDCA that exits the oxidation zone and prior to entry into the solid-liquid separation zone.

Desirably, the pressure drop between the cFDCA feeding the crystallization zone and the crystallized cFDCA exiting the crystallization zone is at least 10 psi, or at least 15 psi, or at least 20 psi, or at least 25 psi, or at least 30 psi, or at least 35 psi, or at least 40 psi, or at least 50 psi, or at least 60 psi, or at least 70 psi.

It is desirable to use more than one crystallization vessel to allow for lower temperature drops across the feed to the particular vessel and the discharge from the same vessel, which in turn allows the crystals to grow to larger sizes. The temperature drop between the feed into a vessel and the discharge of the same vessel is desirably less than 60° C., or no more than 50° C., or no more than 40° C., or no more than 35° C., or no more than 30° C., or no more than 25° C., or no more than 20° C. Desirably, the temperature drop between the feed and discharge of the crystallization vessel is within the metastable region between the solubility value and the supersaturation value at a given feed temperature.

The crude crystallization zone 200 produces a crystallized cFDCA composition 210 which is discharged from the crude crystallization device and fed to the first solid liquid separation zone 300.

The concentrated cFDCA is enriched in the concentration of FDCA solids relative to the concentration of FDCA solids in the composition fed to the first solid liquid separation zone. The concentration of solids in the concentrated FDCA composition stream 310 is increased by at least 10%, or at least 20%, or at least 30%, or at least 40%, or at least 50%, or at least 60%, or at least 70%, or at least 80%, or at least 90%, or at least 100%, or at least 125%, or at least 150%, relative to the concentration of FDCA in the feed to the solid liquid separation zone, based on the weight of the compositions.

In a third step, concentrated cFDCA composition is fed to a dissolution zone in which a hydrogenation solvent composition is combined with the FDCA solids in the concentrated cFDCA composition and at least a portion of the FDCA solids are dissolved in the hydrogenation solvent to thereby produce a solvated FDCA composition (sFDCA) comprising dissolved furan 2,5-dicarboxylic acid (FDCA), a hydrogenation solvent, and 5-formyl furan-2-carboxyic acid (FFCA).

The concentrated cFDCA composition stream 310 is fed to a dissolution zone 400. In the dissolution zone 400, at least a portion of the FDCA solids, whether as a dry powder, wet cake, or in a slurry, are dissolved in a hydrogenation solvent composition at elevated temperatures to form a solvated FDCA composition (sFDCA) stream 410. The hydrogenation solvent composition desirably comprises a solvent which dissolves at least a portion of the FDCA solids under conditions used in the hydrogenation reaction zone and which does not itself convert to other products which must be separated in any appreciable amount, e.g more than 20% conversion of the types of products requiring removal. Suitable hydrogenation solvent compositions include water and steam. Desirably, the hydrogenation solvent composition comprises at least 80 wt. % water, or at least 90 wt. % water, or at least 95 wt. % water, or at least 99 wt. % water, or at least 100 wt. % water.

In the dissolution zone 400, it may be necessary to elevate the temperature of the FDCA solids when combined with the hydrogenation solvent composition to dissolve at least a portion of the FDCA solids into the hydrogenation solvent composition. The hydrogenation solvent and washed FDCA solids are desirably combined at a solvent-to-solids weight ratio in the range of from about 0.5:1 to about 50:1, or in the range of from 1:1 to 20:1, or in the range of from 1:1 to 15:1, or in the range of from 1:1 to 10:1, or in the range of from 1.5:1 to 5:1. The solvated FDCA composition discharged from the dissolution zone can contain hydrogenation solvent, such as water, in an amount ranging from at least 60 wt. %, or at least 70 wt. %, or at least 80 wt. % and up to 99 wt. %, or up to 95 wt. %, or up to 90 wt. %.

Suitable dissolution temperatures are those effective to dissolve the desired amount of FDCA solids into solution. The hydrogenation solvent composition may be added at (by pre-heating) or heated in the dissolution zone to a temperature of at least 120° C. under a pressure and time sufficient to allow for at least 80 wt. % dissolution, although to reduce the time required for dissolution, it is desirable that the hydrogenation solvent composition temperature is at least 130° C., or at least 135° C., or at least 140° C., or at least 150° C. The hydrogenation solvent temperature does not need to exceed 240° C., or 220° C., or 200° C., or even 190° C., or even 180° C. The solubility of FDCA in water at ambient pressure increases dramatically as the temperature of the water increases beyond 130° C.

It is desired to dissolve at least 80 wt. %, or at least 90 wt. %, or at least 95 wt. %, or at least 98 wt. %, or at least 99 wt. % or at least 99.5 wt. % of the solids in the cFDCA solution to produce a the solvated FDCA composition. The sFDCA composition comprises dissolved furan 2,5-dicarboxylic acid (FDCA), the hydrogenation solvent composition, and 5-formyl furan-2-carboxyic acid (FFCA).

An example of the sFDCA composition is:
a) less than 5 wt. %, or less than 4 wt. %, or less than 3 wt. %, or less than 2 wt. %, or less than 1 wt. %, or less than 0.5 wt. %, or less than 0.1 wt. %, or less than 0.01 wt. % solids;
b) dissolved FDCA in an amount of greater than 0, or at least 1 wt. %, or at least 2 wt. %, or at least 5 wt. %, or at least 7 wt. %, or at least 9 wt. %, or at least 10 wt. %, or at least 12 wt. %, or at least 15 wt. %, based on the weight of the sFDCA composition. The upper limit is not particularly limited, but amount of up to 50 wt. %, or up to 45 wt. %, or up to 40 wt. %, or up to 35 wt. %, or up to 30 wt. %, or up to 25 wt. %, or up to 20 wt. %, or up to 15 wt. %, or up to 12 wt. %, based on the weight of the sFDCA composition, are useful; and
c) a hydrogenation solvent in an amount of at least 30 wt. %, or at least 35 wt. %, or at least 40 wt. %, or at least 45 wt. %, or at least 50 wt. %, or at least 55 wt. %, or at least 55 wt. %, or at least 60 wt. %, or at least 65 wt. %, or at least 70 wt. %, or at least 75 wt. %, or at least 80 wt. %, and up to 98 wt. %, or up to 95 wt. %, or up to 92 wt. %, or up to 90 wt. %, or up to 85 wt. %, or up to 80 wt. %, or up to 75 wt. %, or up to 70 wt. %, or up to 65 wt. %, or up to 60 wt. %, or up to 55 wt. %, or up to 50 wt. %, based on the weight of the sFDCA composition; and
d) FFCA in an amount of at least greater than 0, or at least 0.005 wt. % FFCA, or at least 0.01 wt. % FFCA, or at least 0.05 wt. % FFCA, or at least 0.1 wt. % FFCA, or at least 0.25 wt. % FFCA, based on the weight of the sFDCA composition. There is not particular upper limit and the amount can contain 3 wt. % or less, or up to 2.5 wt. %, or up to 2 wt %, or up to 1.5 wt. %, based on the weight of the sFDCA composition.

One advantage of the invention is that FDCA solubilizes in water at much low temperatures, thereby reducing the energy requirements for obtaining a solution adequate for hydrogenation. Although good solubility is also obtained at very high hydrogenation solvent temperatures, it is not necessary to employ such high temperatures to obtain a solution. Thus, the hydrogenation solvent temperature does not need to exceed 240° C., or even 200° C., or even 190° C., or even 180° C. to obtain a solvated FDCA solution. The solvated FDCA solution fed into the hydrogenation reaction zone within the hydrogenation reactor can be at a temperature within the range of 130° C.-200° C., or 135° C.-200° C., or 140° C.-200° C., or 145° C.-200° C., or 150° C.-200° C., or 130° C.-190° C., or 135° C.-190° C., or 140° C.-190° C., or 145° C.-190° C., or 150° C.-190° C., or 130° C.-185° C., or 135° C.-185° C., or 140° C.-185° C., or 145° C.-185° C., or 150° C.-185° C., or 130° C.-180° C., or 135° C.-180° C., or 140° C.-180° C., or 145° C.-180° C., or 150° C.-180° C., or 130° C.-175° C., or 135° C.-175° C., or 140° C.-175° C., or 145° C.-175° C., or 150° C.-175° C.

It is also desirable to provide shear force in the dissolution zone through an impeller or agitator or mechanical mixer to assist with dissolution. The residence time should be sufficient under the temperature and shear conditions to dissolve the FDCA solids to the desired level.

The FDCA solids are contacted with the hydrogenation solvent for a sufficient time, shear, and temperature in the dissolution zone to accomplish dissolving at least a portion of the solids present in crude FDCA. Additionally, to further assist with dissolution, the concentrated FDCA composition stream 310 can be pre-mixed with steam before its introduction into the dissolution vessel. Alternatively, a concentrated FDCA composition stream can be contacted with steam within the dissolution vessel.

In a fourth step, the sFDCA composition is subjected to a hydrogenation reaction in a hydrogenation reaction zone 500 under conditions sufficient to cause hydrogenation of at least a portion of FFCA, and desirably also at least a portion of the color bodies, to generate a hydrogenated FDCA composition ("hFDCA") containing dissolved FDCA and hydrogenation solvent. Hydrogenation converts FFCA and other impurities present in sFDCA composition stream 410 to water soluble compounds.

Desirably, the sFDCA composition can be exposed to hydrogenation conditions in a hydrogenation zone 500 at a temperature within a range of 130° C. to 240° C. by contacting the sFDCA composition with hydrogen 520 in the presence of a hydrogenation catalyst under a hydrogen partial pressure within a range of 10 psig to 900 psig, to thereby produce a hydrogenated furan 2,5-dicarboxylic acid composition (hFDCA) comprising dissolved FDCA, hydrogenated FFCA, and the hydrogenation solvent. In the process of the invention, the cFDCA is purified by catalytic hydrogenation of the by-products in the following non-limiting types of reactions:

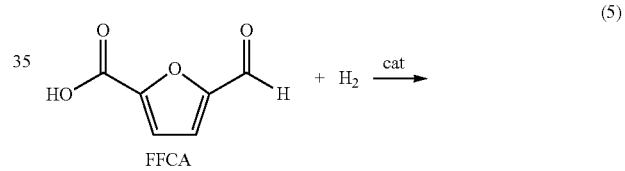

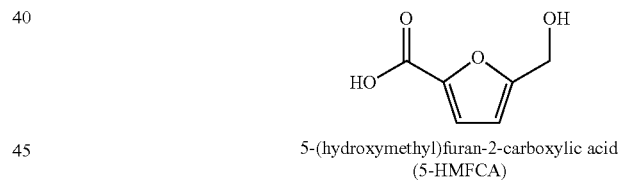

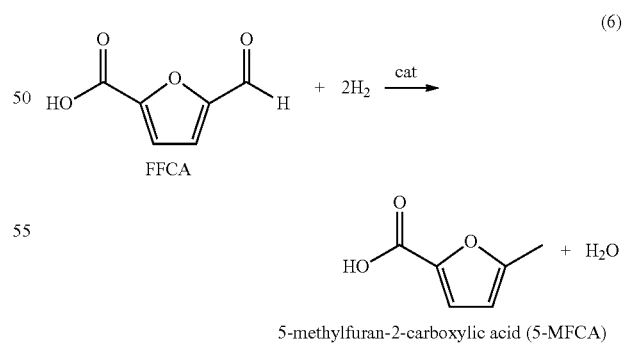

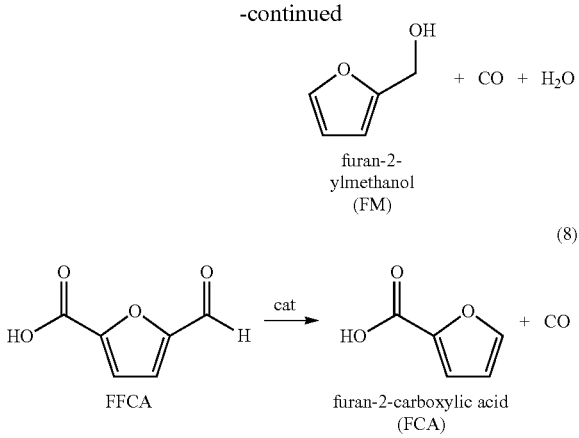

(8)

As can be seen in the reaction equations above, the intermediate FFCA is converted to 5-HMFCA, 5-MFCA, FCA and FM, all of which are water soluble and can be separated easily from FDCA through any number of techniques, such as crystallization in which FDCA precipitates while retaining 5-HMFCA, 5-MFCA, FCA and/or FM in the hydrogenation solvent phase (e.g. aqueous phase). In addition, unsaturation in the colored bodies are converted to saturated species to thereby remove color, and they can either be removed from the product FDCA or can remain in or on the FDCA product.

The sFDCA solution is introduced into a hydrogenation vessel where the solution is contacted, in the hydrogenation reaction zone, with hydrogen 520 and a hydrogenation catalyst. In the process of the invention, hydrogenation is carried out under mild conditions while effectively and dramatically reduce the amount of FFCA and color bodies. By carrying out hydrogenation under mild conditions, selective hydrogenation can be conducted to minimize hydrogenating the furan ring of the FDCA molecule while selectively hydrogenating FFCA and color bodies, compared to conducting hydrogenation under higher temperature and pressure. Further, less energy is consumed to obtain a desired level of intermediate species which result in chain termination and to obtain the desired level of color in the final product. A further advantage of carrying out hydrogenation under mild conditions is the diminished risk of degrading the FDCA molecule.

Unlike conventional hydrogenation process is carried out at a temperature of at least 250° C., in the present invention, hydrogenating the sFDCA solution at a temperature within a range of 130° C. to 240° C., or even less than 200° C., is effective to obtain the desired level of FFCA and color reduction. The hydrogenation temperature in the hydrogenation reaction zone can be at a temperature within a range of 130°-240° C., or 130° C.-225° C., or 130° C.-205° C., or 130° C.-200° C., or 130° C. to less than 200° C., or 135° C. to less than 200° C., or 140° C. to less than 200° C., or 145° C. to less than 200° C., or 150° C. to less than 200° C., or 130°-195°, or 135°-195°, or 140°-195°, or 145°-195°, or 150°-195°, or 130° C.-190° C., or 135° C.-190° C., or 140° C.-190° C., or 145° C.-190° C., or 150° C.-190° C., or 130° C.-185° C., or 135° C.-185° C., or 140° C.-185° C., or 145° C.-185° C., or 150° C.-185° C., or 130° C.-180° C., or 135° C.-180° C., or 140° C.-180° C., or 145° C.-180° C., or 150° C.-180° C., or 130° C.-175° C., or 135° C.-175° C., or 140° C.-175° C., or 145° C.-175° C., or 150° C.-175° C. The hydrogenation temperature is determined by the temperature of the liquid at or near the liquid discharge port of the hydrogenation reactor in a continuous process or by a thermocouple within the liquid inside the hydrogenation reactor in a batch process.

The partial pressure of hydrogen in the hydrogenation reaction zone within the hydrogenation reactor is also reduced to thereby consume less hydrogen while maintaining a good reduction of FFCA and color in the resulting purified FDCA. The partial pressure of hydrogen in the hydrogenation zone is desirably sufficient to drive at least a portion of the hydrogen into solution. In addition, the partial pressure selected is dependent upon the reaction temperature selected. To avoid hydrogenating the furan ring, the partial pressure of hydrogen should be controlled at a given reaction temperature. A lower hydrogen partial pressure should be selected if the reaction temperature is at a high, while higher hydrogen partial pressures can be selected if the reaction temperature is low. The particular values selected within each of the pressure and temperature ranges disclosed above should be effective to lower the b* color and presence of FFCA while minimizing formation of THFDCA (the hydrogenated FDCA ring). The partial pressure of hydrogen can vary from 10 psi to 1000 psi, or from 20 psi to 1000 psi, or from 50 psi to 1000 psi, or from 10 psi to 950 psi, or from 20 psi to 950 psi, or from 50 psi to 950 psi, or from 10 psig to 900 psi, or from 20 psi to 900 psi, or from 50 psi to 900 psi, or from 20 psi to 750 psi, or from 50 psi to 750 psi, or from 20 psi to 600 psi, or from 50 psi to 600 psi, or from 20 psi to 500 psi, or from 50 psi to 500 psi, or from 20 psi to 400 psi, or from 50 psi to 400 psi, or from 20 psi to 300 psi, or from 50 psi to 300 psi, or from 20 psi to 250 psi, or from 50 psi to 250 psi, or from 20 psi to 200 psi, or from 50 psi to 200 psi, or from 20 psi to 150 psi, or from 50 psi to 150 psi, or from 20 psi to 100 psi, or from 50 psi to 100 psi, or from 20 psi to 90 psi, or from 50 psi to 90 psi. The hydrogen partial pressure is calculated by subtracting the vapor pressure of water or combination of hydrogenation solvents at the reaction temperature from the total reactor pressure.

The total pressure within the hydrogenation reaction zone is also desirably effective to provide a reduction of FFCA and color in the resulting purified FDCA without formation of high amounts of THFDCA while also sufficient to drive the hydrogen into solution. The total pressure can vary from 35 psig to 1200 psig, or from 50 psig to 1200 psig, or from 35 psig to 1000 psig, or from 50 psig to 1000 psig, or from 35 psig to less than 950 psig, or from 50 psig to less than 950 psig, or from 70 psig to less than 950 psig, or from 35 psig to 930 psig, or from 50 psig to 930 psig, or from 70 psig to 930 psig, or from 35 psig to 900 psig, or from 50 psig to 900 psig, or from 70 psig to 900 psig, or from 35 psig to 800 psig, or from 50 psig to 800 psig, or from 70 psig to 800 psig, or from 35 psig to 650 psig, or from 50 psig to 650 psig, or from 70 psig to 650 psig, or from 35 psig to 550 psig, or from 50 psig to 550 psig, or from 70 psig to 550 psig, or from 35 psig to 350 psig, or from 50 psig to 350 psig, or from 70 psig to 350 psig, or from 35 psig to 300 psig, or from 50 psig to 300 psig, or from 70 psig to 300 psig, or from 35 psig to 250 psig, or from 50 psig to 250 psig, or from 70 psig to 250 psig, or from 35 psig to 200 psig, or from 50 psig to 200 psig, or from 70 psig to 200 psig, or from 35 psig to 150 psig, or from 50 psig to 150 psig, or from 70 psig to 150 psig, or from 35 psig to 130 psig, or from 50 psig to 130 psig, or from 70 psig to 130 psig.

The molar ratio of hydrogen fed to the hydrogenation reaction zone to moles of sFDCA fed to the hydrogenation zone is desirably in the range of from 0.01:1 to 2:1, or 0.02:1 to 1:1, or from 0.02:1 to less than 1:1, or from 0.02:1 to 0.8:1, or from 0.02:1 to 0.5:1, or from 0.02:1 to 0.1:1, or from 0.02:1 to 0.08:1, or from 0.02:1 to 0.06:1.

Hydrogen can be fed into the hydrogenation reaction zone pure at a 100 mole % hydrogen concentration or as a mixed feed with other inert gases. The concentration of hydrogen fed into the reaction zone is not particularly limited. Suitable amounts can be at least 80 wt. %, or at least 90 wt. %, or at least 95 wt. %, or at least 98 wt. %, or at least 99.5 wt. %.

The residence time is effective to reduce the b* color of the sFDCA composition and reduce the amount of FFCA while minimizing the formation of THFDCA at the reaction temperature and catalyst type and loading selected. Examples of suitable residence times of the sFDCA in the hydrogenation reaction zone can range from 15 minutes to 10 hours, and 45 minutes to about 5 hours are useful and commercially practical.

The process of the present invention can be operated in a variety of configurations or vessel designs. One such configuration or vessel is a fixed bed flow reaction system. Desirably, the hydrogenation reaction is conducted in a fixed bed flow reaction system. The substrate to be hydrogenated, the sFDCA solution, is in the dissolved phase in the hydrogenation reaction zone. Another type of suitable configuration or vessel is a trickle bed configuration or a stirred tank reactor. Regardless of the method of operation, the desired time of contact between the sFDCA solution, hydrogen, and catalyst components can be varied as desired to achieve the desired level of reaction.

One example is a hollow cylindrical vessel that is vertically oriented, in which the sFDCA solution is introduced into the hydrogenation reactor at or near the top of the vessel and in the presence of hydrogen flows down through the reaction chamber or zone and over a fixed catalyst bed supported by mesh, wire, or perforated plates. The hydrogenated FDCA solution is discharged from the hydrogenation reactor at or near the bottom of the reactor. The reactor can be dissolved full or may have a gas head above the dissolved level of the sFDCA solution, but the dissolved level should at least submerge the catalyst beds. If not dissolved full, the reactor can be operated to maintain a constant dissolved level by feeding hydrogen gas into the gas space at a rate sufficient to maintain a constant dissolved level. If operated dissolved full, the hydrogen can be dissolved in at least a portion of the sFDCA solution with a flow meter and fed into the hydrogenation reaction zone as a dissolved hydrogen FDCA solution.

The sFDCA solution is contacted with a hydrogenation catalyst in the hydrogenation reaction zone. Any conventional hydrogenation catalyst may be employed. The hydrogenation catalyst employed in the hydrogenation zone/vessel can be a noble Group VIII metal on a conventional catalyst carrier or support material such as carbon. Although palladium on carbon is a typical hydrogenation catalyst, it is possible to use catalysts containing other platinum group metals such as ruthenium, rhodium, osmium, iridium and platinum, or an oxide of such a metal or by a metallic catalyst like Pd and/or Rh on carbon. It is also possible to use layered catalyst beds consisting of a layer of Rh on carbon catalyst before or after the bulk of Pd on carbon catalysts.

The carbon support material can be granular, in pellet form, or any other particle form. The type of carbon used is also not limited. Activated carbon can be used having a surface area of at least 200 m$^2$/gm without any upper limit. Suitable amounts can range from 200 to 3000 m$^2$/gm, or from 300 to 3000 m$^2$/gm, or from 500 to 3000 m$^2$/gm or from 600 to 3000 m$^2$/gm, each by the BET Method.

The loading of metal onto the support can be from 0.01 wt. % up to 5 wt. %, or from 0.01 to 1.0 wt. %, based on the weight of the final catalyst composition (including the support). The amount of catalyst metal loaded into the reaction zone is effective to obtain the desired degree of conversion without excessive production of by-products. The moles of FFCA fed into the hydrogenation reactor per hour to the moles of total catalyst metal(s) employed can be at least 0.1 hr$^{-1}$:1, or at least 1 hr$^{-1}$:1, or at least 5 hr$^{-1}$:1, or at least 10 hr$^{-1}$:1, and can be as high as desired although consideration should be given to avoid an excessive amount of total catalyst metal(s) that could lead to the formation of excessive amounts of THFDCA. Suitable molar ratios of FFCA fed per hour to moles of catalyst metal can be up to 150 hr$^{-1}$:1, or up to 125 hr$^{-1}$:1, or up to 100 hr$^{-1}$:1.

The hydrogenation reactor can be any conventional hydrogenation vessel. One example is a hollow cylindrical vessel that horizontally or vertically oriented, desirably is vertically oriented, in which the sFDCA solution is introduced into the hydrogenation reactor at or near the top of the vertical vessel or at one end of a horizontal vessel, and in the presence of hydrogen flows down through the reaction chamber or zone and over a fixed catalyst bed supported by mesh, wire, or perforated plates in a vertical vessel or across the catalyst bed in a horizontally oriented reactor. The hydrogenated FDCA solution is discharged from the hydrogenation reactor at or near the bottom of the reactor in a vertical reactor or at an end that is distal from the entry point in a horizontally oriented reactor. The reactor can be liquid full or may have a gas head above the liquid level of the sFDCA solution, but the liquid level should at least submerge the catalyst beds. If not liquid full, the reactor can be operated to maintain a constant liquid level by feeding hydrogen gas into the gas space at a rate sufficient to maintain a constant liquid level. If operated liquid full, the hydrogen can be dissolved in at least a portion of the sFDCA solution with a flow meter and fed into the hydrogenation reaction zone as a dissolved hydrogen FDCA solution.

During the hydrogenation process, the following undesired reactions in equations 9, 10, or 11 may occur if the hydrogenation conditions are too severe, either because the hydrogenation temperature is too high for the residence time (or average hourly space velocity) employed, or the partial pressure of hydrogen is too high, or the catalyst loading is too high, or a combination of two or more of these activities:

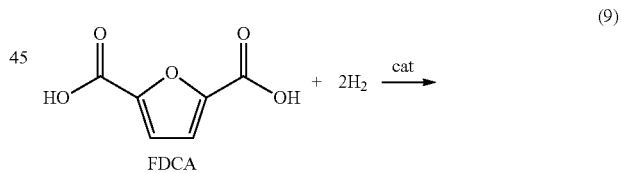

(9)

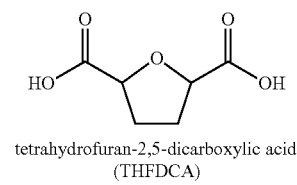

tetrahydrofuran-2,5-dicarboxylic acid (THFDCA)

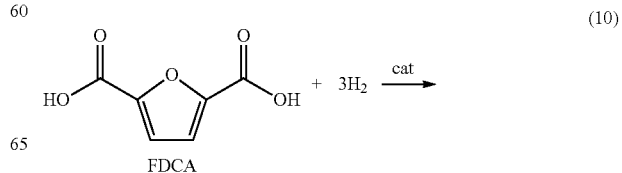

(10)

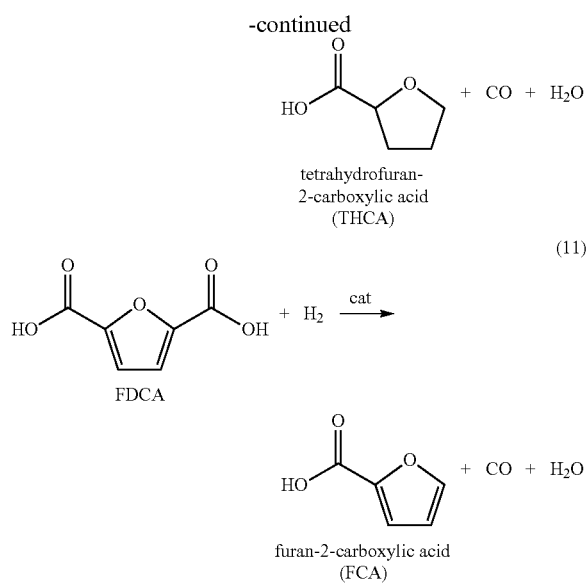

tetrahydrofuran-
2-carboxylic acid
(THCA)

(11)

FDCA furan-2-carboxylic acid
(FCA)

Hydrogenating under conditions that are too severe results in hydrogenating the furan ring, or dissociating a carboxylic acid group from the furan ring, or a combination of both. Thus, it is desirable to conduct the hydrogenation reaction under conditions effective such that the hydrogenated FDCA composition (hFDCA) discharged from the hydrogenation reaction zone contains no more than 2 wt. % of THFDCA, or no more than 1.5 wt. %, or no more than 1 wt. %, or no more than 0.8 wt. %, or no more than 0.7 wt. %, or no more than 0.6 wt. %, or no more than 0.5 wt. %, or no more than 0.4 wt. %, or no more than 0.3 wt. %, or no more than 0.1 wt. % THFDCA, based on the weight of the hFDCA composition, which includes liquid and solids. While higher amounts of THFDA can be contained within the hFDCA composition, such as less than 10 wt. % THFDCA, or no more than 5 wt. % THFDCA and greater than 2 wt. %, based on the weight of the hFDCA composition, such high amount of THFDCA represent a high loss of yield, and a commercial process would become impractical to maintain.

In a fifth step, the hFDCA composition is crystallized to generate a crystallized hFDCA composition comprising liquid and FDCA solids.

The hFDCA composition 510 is fed to a purified crystallization zone 600 in which the hFDCA composition is subjected to crystallization conditions to form a crystallized hFDCA composition 610. Feeding the hFDCA composition to a purified crystallization zone 600 has the advantage of generating a larger amount of FDCA solids by precipitating into the solid phase any FDCA in the liquid phase of the hFDCA composition, while leaving other hydrogenated impurities in the hydrogenation solvent phase (e.g. aqueous phase). It also has the advantage of lowering the temperature of the hFDCA stream by evaporative cooling through pressure reduction so that the solid-liquid separator is not subjected to the extreme high temperatures and pressures of the cFDCA composition exiting the hydrogenation reaction zone 500. The decreased temperature in crystallization system causes the majority (more than 50 wt. %, or at least 75 wt. %, or at least 80 wt. %, or at least 90 wt. %, or at least 95 wt. %, or at least 98 wt. %, or at least 99 wt. %) of the dissolved FDCA in the hFDCA composition stream 510 to precipitate and form solids.

Generally, the purified crystallization zone 600 comprises at least one crystallizer. The off-gas from the crystallizer is a vapor composition stream 620 that can be condensed in at least one condenser and returned to the purified crystallization zone 600. Optionally, the liquid from the condenser or vapor product from the purified crystallization zone 600 can be recycled to the primary oxidation zone 100, or it can be withdrawn or sent to an energy recovery device. In addition, the vapor composition removed via line 620 can be routed to a recovery system where the oxidation solvent is removed and remaining VOCs may be treated, for example by incineration in a catalytic oxidation unit.

Figure 2:
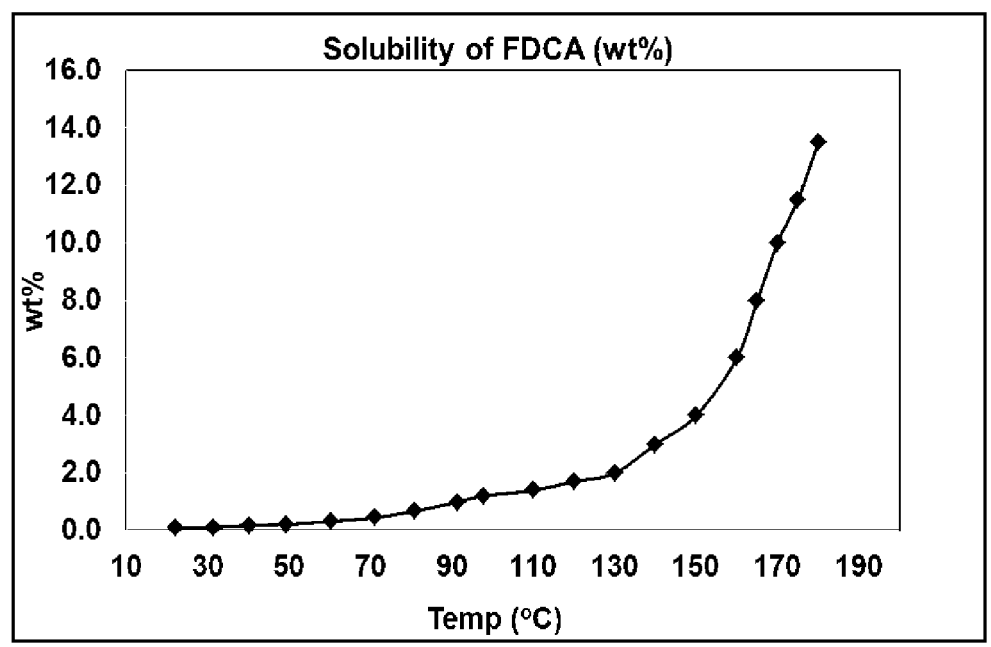
FIG. 2 depicts the solubility of FDCA in water at different temperatures.

The crystallized hFDCA stream is at a temperature that is at least 15° C., or at least 20° C., or at least 30° C., or at least 40° C., or at least 50° C., or at least 60° C., or at least 70° C., or at least 80° C. lower than the temperature of the hFDCA composition fed to the purified crystallization zone 600. Desirably, the crystallized hFDCA composition 610, either as discharged from the purified crystallization zone 600 or as introduced into the second solid-liquid separation zone 700, is at a temperature of 130° C. or less, or 120° C. or less, or 110° C. or less, or less than 100° C., or 99° C. or less, of 95° C. or less, or 80° or less, or 70° C. or less, or 60° C. or less. Cooling the hFDCA composition to obtain a crystallized hFDCA composition 610 at a temperature below 130° C. when the hydrogenation solvent is water has the advantage of crystallizing increasing amounts of dissolved FDCA as can be seen from the solubility curve of FDCA in water in FIG. 2. Cooling below the boiling point of water of 100° C. has the advantage of avoiding flashing water in a vacuum solid liquid separation device.

The hFDCA composition can be cooled in at least one crystallization vessel to a temperature that is at least 10° C., or at least 20° C., or at least 30° C. lower than the temperature of the hFDCA composition fed to that same vessel. It is desirable to use more than one crystallization vessel to allow for lower temperature drops across the feed to the particular vessel and the discharge from the same vessel, which in turn allows the crystals to grow to larger sizes. The temperature drop between the feed into a purified crystallization vessel and the discharge of the same vessel of at least one of the vessels within the purified crystallization zone, and desirably all the vessels, can be less than 60° C., or no more than 50° C., or no more than 40° C., or not more than 35° C., or not more than 30° C., or not more than 25° C., or not more than 20° C., or not more than 15° C., but at least 5° C.

Desirably, the temperature within at least one purification crystallization vessel is with a range of 40° C. to 160° C., or 50° C. to 150° C., or 60° C. to 140° C.

One method for cooling the hFDCA composition stream 510 is flashing the hydrogenation solvent to a vapor by pressure reduction within the purified crystallizer zone 600. The pressure can be let down, and the temperature reduced, within the purified crystallization zone 600 in stages using more than one crystallization vessel. Although flash cooling by pressure reduction has been described above, the hFDCA composition can be cooled by any method known in art.

One method for cooling the hFDCA composition stream 510 can be accomplished by operating the purified crystallization zone 600 under a pressure that is lower than pressure of the hFDCA composition feeding the purified crystallization zone 600. Means for lowering the pressure include allowing the hFDCA stream to be fed into one or more flash vessels operated at or above ambient pressure or at or above 1 atm., a crystallization vessel that is operated under a vacuum of less than 1 atm, cooling coils such as would be found in a heat exchanger, or a combination of these means. Desirably, at least one of the purified crystallization vessels is a flash vessel operated at or above 1 atm. Desirably, in addition to one or more flash vessels, one may use one or more crystallization vessels operated under a vacuum of less than 1 atm. while simultaneously flashing at least a portion of the cFDCA fed to the vessel, optionally also operating as a mechanically stirred tank.

It is also desirable, if more than one purified crystallization vessel is employed in series, for the pressure within a downstream purified crystallization vessel to be lower than the pressure of at least one purified crystallization vessel upstream in the series, and even more desirable is that the pressure within each purified crystallization vessel is lower with each downstream successive vessel in the series. The pressure reduction from the feed inlet to the discharge within at least one crystallization vessel, and desirably the pressure differential of at least two vessels, and more desirably the pressure differential of each successive crystallization vessel in the series (comparing the operating pressure of one vessel to another vessel and taking the difference), can be at least 10 Torr, or at least 20 Torr, or at least 30 Torr, or at least 50 Torr, or at least 100 Torr. One or more of the crystallizer vessels can be a mechanically stirred tank.

Taking as an example, 4 vessels operated in series within the purified crystallization zone, the first vessel in the purified crystallization zone can be a flash tank operated under ambient or at least 1 atm, the second vessel can be a another flash tank operated under ambient or at least 1 atm., the third vessel can be a flash evaporation crystallizer vessel operated under a vacuum of 750 Torr absolute or less or 400 Torr absolute or less with a feed inlet above the liquid level within the vessel that introduces the hFDCA feed into the vessel, desirably across a pressure drop (such as a valve or pipe constriction) to flash the oxidation solvent, and the fourth vessel can be a crystallizer vessel, optionally operated with flash evaporation, under an additional vacuum such as 200 Torr absolute or less.

Since the pressure drops will volatize or flash the oxidation solvent, thereby producing a crystallized hFDCA composition enriched in the concentration of FDCA relative to the concentration of FDCA in the hFDCA composition feeding the purified crystallization zone 600, while also cooling the hFDCA by evaporative cooling and/or applied cooling as by way of cooling tubes, there exists a temperature drop from one purified crystallization vessel to the next succeeding purified crystallization vessel of at least two adjacent vessels. Desirably, the temperature drop differential of at least two adjacent crude purified crystallization vessels in the series, and desirably of each adjacent purified crystallization vessel (which includes a flash tank) in a series, is desirably at least 10° C., or at least 20° C., or at least 30° C. For example in a series of 4 crystallization vessels, the second in the series will be operated at a temperature that is at least 10° C. cooler than the first in the series, and the third in the series will be operated at a temperature that is at least 10° C. cooler than the second, and the fourth will be operated at a temperature that is at least 10° C. cooler than the third in the series. Desirably, the first in the series cools the hFDCA feed also be at least 10° C., although if the first vessel in the series is a flash evaporation tank, the amount of cooling in this tank may be less than 10° C.

Any other method of cooling may be employed in addition to or in place of evaporative cooling and/or cooling tubes, but in any event, there is desirably a pressure drop across the hFDCA that exits the hydrogenation reaction zone and prior to entry into the second solid-liquid separation zone to cool the temperature of the hFDCA composition.

Desirably, the pressure drop between the hFDCA stream 510 feeding the purified crystallization zone 600 and the crystallized hFDCA 610 exiting the purified crystallization zone 600 can be at least 10 psi, or at least 15 psi, or at least 20 psi, or at least 25 psi, or at least 30 psi, or at least 35 psi, or at least 40 psi, or at least 50 psi, or at least 60 psi, or at least 70 psi, or at least 90 psi, or at least 100 psi, or at least 150 psi, or at least 200 psi, or at least 250 psi, or at least 300 psi, or at least 350 psi, or at least 400 psi. A significant portion of the pressure drop can occur in one or more flash vessels within the purified crystallization zone.

In a sixth step, at least a portion of the liquid in the crystallized hFDCA composition 610 is separated from the FDCA solids to thereby generate a purified FDCA composition enriched in the concentration of FDCA solids relative to the concentration of FDCA solids in the crystallized hFDCA composition.

For example, as shown in FIG. 1, the purified crystallization zone 600 produces a concentrated hFDCA solution which is discharged from the purified crystallization device and fed to the second solid liquid separation zone 700 to produce a purified FDCA product composition stream 710 (pFDCA) comprising FDCA solids.

In the second solid liquid separation zone 700, a second mother liquor stream 730 and a second wash liquor stream 740 are generated. These functions may be accomplished in a single solid-liquid separation device or multiple solid-liquid separation devices. The second solid-liquid separation zone comprises at least one solid-liquid separation device capable of separating solids and liquids, and desirably also washing solids with a wash fed stream 720.

The principles of operation, types of devices, and process conditions suitable for use in the second solid liquid separation zone 700 are described above with reference to the first solid liquid separation zone 300.

Consideration to the operating conditions should be given to account for the presence of the hydrogenation solvent. For example, only one wash zone may be required to adequately wash the FDCA cake if the hFDCA composition uses water as the hydrogenation solvent and the wash solvent is also water. The wash solvent composition 720 can be customized to produce a wet cake designed for an end use application. For example, if a dry solid is desired, multiple wash zones can be provided in which the first wash solvent can be water to wash the remaining water soluble impurities from the FDCA solids, followed by an acetic acid wash which, due to its higher vapor pressure, more readily evaporates and dries the FDCA cake with less energy consumption than would be required if the cake was water wet. Alternatively, if one desires to ship a water moist cake, only one wash zone with a water wash is needed, although more can be used, with optional partial drying. Or, if one desires to ship a hydroxyl wet cake, the last wash zone can be with a wash composition containing a compound having at least one hydroxyl group such as methanol or ethylene glycol to produce a methanol wet cake or an EG wet cake. Even when making a dry solids, one may nevertheless wash with water and feed the water wet cake to the dryer to avoid having to separate acetic acid from water in a wash liquor solvent.

Upon separation of at least a portion of the liquid from the FDCA solids in the crystallized hFDCA composition, a purified FDCA composition (pFDCA) is generated that is enriched in the concentration of FDCA solids relative to the concentration of FDCA solids in the crystallized hFDCA composition. The degree of enrichment is dependent upon the form (slurry, wet cake, dried solids) in which one desires to ship and use the pFDCA composition. A suitable increase in the concentration of FDCA solids by weight of the purified FDCA composition relative to the concentration of FDCA solids in the crystallized hFDCA composition by weight of the crystallized FDCA composition can be at least 10%, or at least 20%, or at least 30%, or at least 40%, or at least 50%, or at least 60%, or at least 70%, or at least 80 wt. %, or at least 90%.

If one desired to produce a purified dry FDCA composition as the product, the FDCA cake or cake residue 710 can be fed to an optional dryer zone 800 to generate a dry product stream 810 comprising FDCA solids and vapor stream 820 comprising at least a portion of the wash solvent that remained on the cake 710. Although a solid liquid separator device may come equipped with a drying zone, the moisture content on the discharged cake may not be sufficiently low to meet a customer specification. Therefore, an additional optional dryer in dryer zone 800 may employed to further reduce the moisture content on the cake to produce dried purified FDCA solids having a moisture level of less than 5 wt % moisture, or no more than 4 wt. % moisture, or no more than 3 wt. % moisture, or no more than 2 wt. % moisture, or no more than 1 wt. % moisture, or no more than 5000 ppm moisture, or no more than 1000 ppm moisture, or no more than 500 ppm moisture, based on the weight of the dried purified FDCA solid stream as discharged from the dryer zone 800.

The vapor stream 820 comprises wash solvent used in the second solid liquid separation zone 700 that exits the dryer zone 800 as a vapor. The dryer zone 800 comprises at least one dryer and can be accomplished by any means known in the art that is capable of evaporating at least 10% of the volatiles in the purified FDCA cake stream 710 to produce the dry purified FDCA stream 810 comprising purified FDCA. For example, indirect contact dryers including a rotary steam tube dryer, a Single Shaft Porcupine™ dryer, and a Bepex Solidaire™ dryer. Direct contact dryers including a fluid bed dryer, a ring dryer, and drying in a convey line can be used for drying to produce stream 810.

If desired, a vacuum system can be utilized to pull vapor stream 820 from the dryer zone 800. If a vacuum system is used in this fashion, the pressure of stream 820 at the dryer outlet can range from about 760 mmHg absolute to about 400 mmHg absolute, from about 760 mmHg absolute to about 600 mmHg absolute, from about 760 mmHg absolute to about 700 mmHg absolute, from about 760 mmHg absolute to about 720 mmHg absolute, from about 760 mmHg absolute to about 740 mmHg absolute, wherein pressure is measured in mmHg above absolute vacuum.

The contents of the conduit between second solid-liquid separation zone 700 and the dryer zone 800 utilized to transfer purified FDCA cake stream 810 may contain FDCA solids and gas wherein gas is the continuous phase. In one embodiment, the difference in pressure where cake stream 810 exits the second solid liquid separation zone 700 and where vapor stream 820 exits drying zone 800 is less than 2 psi gauge, less than 0.8 psi gauge, and preferably less than 0.4 psi gauge. In one embodiment, a rotary air-lock valve is used to discharge solids from the dryer zone to a location outside the dryer zone that has a higher pressure than the drying zone. In this embodiment, the rotary air-lock valve serves to meter dry solids from the dryer into a higher pressure environment.

The purified FDCA composition produced by the process of the invention ("pFDCA") desirably has the following composition:

The pFDCA composition desirably has the following composition:
a) solids, wherein at least 95 wt. %, or at least 97 wt. %, or at least 98 wt. %, or at least 99 wt. %, or at least 99.5 wt. %, or at least 99.8 wt. %, or at least 99.9 wt. %, or at least 99.95 wt. % of the solids are FDCA, based on the weight of the solids;
b) a b* of at least zero and less than 4, or less than 3, or less than 2, or less than 1.5, or less than 1, or less than 0.8, or less than 0.5;
c) FFCA in an amount of less than 500 ppm, or less than 200 ppm, or less than 100 ppm, or less than 50 ppm, or less than 25 ppm, or less than 20 ppm, or less than 15 ppm, or no more than 10 ppm;
d) and THFDCA present in an amount ranging from zero, or greater than zero, or at least 1 ppm, or at least 2 ppm, or at least 5 ppm, or at least 10 ppm, or at least 20 ppm, or at least 30 ppm, or at least 50 ppm, and in an amount of no more than 0.5 wt. %, or less than 0.4 wt. %, or less than 0.3 wt. %, or less than 0.1 wt. % THFDCA, or less than 500 ppm, or not more than 100 ppm, or not more than 50 ppm, or not more than 30 ppm, or not more than 25 ppm, or not more than 20 ppm, or not more than 15 ppm, in each case based on the weight of the solids.

In one embodiment, the pFDCA composition desirably comprises at least 98 wt. % solids, or at least 99 wt. % solids, or at least 99.5 wt. % solids, or at least 99.9 wt. % solids, or at least 99.5 wt. % solids. This embodiment would represent an isolated dried solids product.

In another embodiment, the product FDCA composition desirably contains at least 2 wt. % liquid, or at least 4 wt. % liquid, or at least 6 wt. % liquid, and up to 40 wt. % liquid, or up to 30 wt. % liquid, or up to 20 wt. % liquid, or up to 15 wt. % liquid, with the remainder solids, and the solid comprise at least 99 wt. % FDCA and FFC and THFDCA in any of the amounts mentioned above. This embodiment would represent a wet cake product.

A very low b* can be obtained in the purified FDCA composition by hydrogenating the cFDCA composition. The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow). Solid samples of FDCA can be analyzed using a Hunter Lab UltraScan Pro spectrophotometer with an integrating light sphere. Per manufacturer recommendation the spectrophotometer should be set to the CIELAB color scale with the D65 illuminate and 10° observer. The spectrophotometer is standardized in total reflectance mode.

More in particular, the b* can be measured by using a Hunter Ultrascan XE instrument and preparing the samples and conducting the analysis by the following method:
1) Assemble a Carver Press die and place the die on the base and place the bottom 40 mm cylinder polished side face-up.
2) Place a 40 mm plastic cup (Chemplex Plasticup, 39.7× 6.4 mm) into the die.
3) Fill the cup with the sample to be analyzed. The exact amount of sample added is not important.
4) Place the top 40 mm cylinder polished side face-down on the sample.
5) Insert the plunger into the die. No "tilt" should be exhibited in the assembled die.
6) Place the die into the Carver Press, making sure that it is near the center of the lower platen. Close the safety door.
7) Raise the die until the upper platen makes contact with the plunger. Apply >20,000 lbs pressure. Then allow the die to remain under pressure for approximately 3 minutes (exact time not critical).

8) Release the pressure and lower the lower platen holding the die.
9) Disassemble the die and remove the cup. Place the cup into a labeled plastic bag (Nasco Whirl-Pak 4 oz).
10) Using a HunterLab Colorquest XE colorimeter, create the following method (Hunterlab EasyQuest QC software, version 3.6.2 or later):
    Mode: RSIN-LAV (Reflectance Specular Included-Large Area View, 8° viewing angle)
    Measurements:
    CIE L* a* b*
    CIE XYZ
11) Standardize the instrument as prompted by the software using the light trap accessory and the certified white tile accessory pressed against the reflectance port.
12) Run a green tile standard using the certified white tile and compare the CIE X, Y, and Z values obtained against the certified values of the tile. The values obtained should be ±0.15 units on each scale of the stated values.
13) Analyze the sample in the bag by pressing it against the reflectance port and obtaining the spectrum and L*, a*, b* values. Obtain duplicate readings and average the values for the report.

The process of the invention can be operated on a commercial scale. Examples of suitable rates for the production of a pFDCA composition include an average of at least 1,000 kg/day, or at least 10,000 kg/day, or at least 20,000 kg/day, or at least 50,000 kg/day, or at least 75,000 kg/day, or at least 100,000 kg/day, or at least 200,000 kg/day of a pFDCA composition on a solids basis, on a 24 hour basis over the course of any three months.

The pFDCA composition, which can be either dried carboxylic acid solids or wet cake, comprising FDCA can be fed to an esterification reaction zone. The pFDCA composition can be shipped via truck, ship, or rail as solids.

The process for making the pFDCA composition can be integrated with the process for the manufacture of an esterification facility to make a diester or a polyester. An integrated process includes co-locating the two manufacturing facilities, one for hydrogenation, and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a dissolved slurry to the facility for esterification.

The invention has been described in detail with particular reference to preferred embodiments thereof, but will be understood that variations and modification can be affected within the spirit and scope of the invention.

What we claim is:

1. A furan-2,5-dicarboxylic acid (FDCA) composition comprising:
    a) solids, wherein at least 95 wt. % of the solids are FDCA;
    b) a b* value of 0 to less than 4;
    c) 5-formyl furan-2-carboxyic acid (FFCA) in an amount of less than 500 ppm; and
    d) tetrahydrofuran-2,5-dicarboxylic acid (THFDCA) present in an amount ranging from zero to no more than 0.5 wt. %;
    in each case based on the weight of the solids.

2. The composition of claim 1, wherein the composition comprises at least 98 wt. % solids.

3. The composition of claim 2, comprising:
    a) solids, wherein at least 99 wt. % of the solids are FDCA;
    b) a b* value of 0 to less than 3;
    c) FFCA in an amount of less than 50 ppm; and
    d) THFDCA present in an amount ranging from zero to no more than 0.1 wt. %;
    in each case based on the weight of the solids.

4. The composition of claim 3, comprising THFDCA present in an amount ranging from zero to no more than 500 ppm, based on the weight of the solids.

5. The composition of claim 4, comprising:
    a) solids, wherein at least 99.5 wt. % of the solids are FDCA;
    b) a b* value of 0 to less than 3;
    c) FFCA in an amount of less than 25 ppm; and
    d) THFDCA present in an amount ranging from zero to no more than 50 ppm;
    in each case based on the weight of the solids.

6. The composition of claim 5, comprising:
    a) solids, wherein at least 99.5 wt. % of the solids are FDCA;
    b) a b* value of 0 to less than 2;
    c) FFCA in an amount of less than 25 ppm; and
    d) THFDCA present in an amount ranging from zero to no more than 25 ppm;
    in each case based on the weight of the solids.

7. The composition of claim 6, comprising at least 99.5 wt. % solids.

8. The composition of claim 1, wherein the composition contains 4 wt. % to 40 wt. % liquid.

9. The composition of claim 1, wherein said composition is fed to an esterification reaction zone.

10. The composition of claim 1, wherein said composition is isolated and shipped by truck, ship, or rail.

* * * * *